(12) United States Patent
Jacoby

(10) Patent No.: US 8,684,732 B2
(45) Date of Patent: Apr. 1, 2014

(54) SYSTEM AND METHOD FOR PREVENTION AND TREATMENT OF PERI-IMPLANT INFECTION

(76) Inventor: Bennett Jacoby, Sioux Falls, SD (US)

( * ) Notice: Subject to any disclaimer, the term of this patent is extended or adjusted under 35 U.S.C. 154(b) by 0 days.

(21) Appl. No.: 13/313,549

(22) Filed: Dec. 7, 2011

(65) Prior Publication Data
US 2012/0156645 A1 Jun. 21, 2012

Related U.S. Application Data

(60) Provisional application No. 61/423,455, filed on Dec. 15, 2010.

(51) Int. Cl.
*A61C 8/00* (2006.01)

(52) U.S. Cl.
USPC ........................................... 433/173

(58) Field of Classification Search
USPC .................................. 433/174, 175
See application file for complete search history.

(56) References Cited

U.S. PATENT DOCUMENTS

| | | | |
|---|---|---|---|
| 779,516 A * | 1/1905 | Armstrong ........................ 83/14 |
| 4,872,840 A | 10/1989 | Bori |
| 5,145,372 A * | 9/1992 | Daftary et al. ................. 433/173 |
| 5,152,687 A | 10/1992 | Amino |
| 5,322,443 A * | 6/1994 | Beaty ............................ 433/141 |
| 5,431,567 A | 7/1995 | Daftary |
| 5,915,967 A | 6/1999 | Clokie |
| 5,961,329 A * | 10/1999 | Stucki-McCormick ...... 433/173 |
| 6,050,819 A | 4/2000 | Robinson |
| 6,220,861 B1 | 4/2001 | Kwon et al. |
| 6,537,070 B1 | 3/2003 | Stucki-McCormick |
| 6,726,481 B1 | 4/2004 | Zickmann et al. |
| 6,733,292 B2 | 5/2004 | Odrich et al. |
| 6,743,018 B1 | 6/2004 | Morrow |
| 6,824,384 B1 * | 11/2004 | Bompard et al. ............... 433/75 |
| 6,939,135 B2 | 9/2005 | Sapian |
| 7,179,084 B1 * | 2/2007 | Kometas ......................... 433/75 |
| 7,281,926 B2 * | 10/2007 | Yakir ............................ 433/176 |
| 7,303,396 B2 | 12/2007 | Abarno |
| 7,780,448 B2 | 8/2010 | Kim |
| 8,152,848 B2 * | 4/2012 | Freilich et al. ............. 623/16.11 |
| 2003/0165795 A1 | 9/2003 | Stucki-McCormick |
| 2005/0084822 A1 | 4/2005 | Stucki-McCormick |
| 2007/0105068 A1 | 5/2007 | Stucki-McCormick |
| 2007/0148621 A1 * | 6/2007 | Yakir ............................ 433/173 |
| 2007/0172796 A1 | 7/2007 | Hyun et al. |
| 2008/0118893 A1 * | 5/2008 | Armellini et al. ............. 433/174 |
| 2008/0213728 A1 | 9/2008 | Rhew |
| 2009/0036908 A1 * | 2/2009 | Zokol et al. ................... 606/151 |
| 2009/0280454 A1 | 11/2009 | Hanna |
| 2010/0003638 A1 | 1/2010 | Collins et al. |
| 2010/0003640 A1 | 1/2010 | Damstra et al. |
| 2010/0323326 A1 | 12/2010 | Reed |
| 2010/0330534 A1 | 12/2010 | Hyun |
| 2011/0189634 A1 * | 8/2011 | Kfir ............................... 433/174 |

* cited by examiner

*Primary Examiner* — Ralph Lewis
(74) *Attorney, Agent, or Firm* — Brian C. Trask

(57) ABSTRACT

A system, method and device design to prevent, treat and maintain dental periimplant infections including a dental implant to be inserted into a jawbone of a patient that includes a base segment provided at one distal end of the implant which is configured to be put inside and come in contact with the jawbone, an abutment portion provided on an end opposite to the one distal end of the implant to which an artificial tooth is configured to be attached, and a plurality of removable segments which are configured to be put inside and come in contact with the jawbone and are removably attached to the base segment. If an infection is diagnosed around an implant site, infected removable segments can be extracted while maintaining positioning of the uninfected removable segments and the base segment. The infected removable segments are replaced with cleaned or sterilized removable segments.

38 Claims, 28 Drawing Sheets

SYSTEM AND METHOD FOR PREVENTION AND TREATMENT OF PERI-IMPLANT INFECTION

This application claims the benefit pursuant to 35 U.S.C. §119(e)(1) of U.S. Provisional Application No. 61/423,455 filed Dec. 15, 2010, the disclosure of which is incorporated herein in its entirety.

BACKGROUND OF THE INVENTION

The present invention relates to a system and method for prevention and treatment of peri-implant infection.

Dental implants have become the new standard of care for replacement of missing teeth. As shown in FIG. 1, the dental implants consist of a titanium fixture 1 that may either be threaded or unthreaded on the exterior and usually has a sintered surface. The fixture 1 is placed into the jaw bone surgically by drilling a hole in the bone and screwing or tapping the fixture in, or it is simply screwed into a fresh tooth extraction site. This fixture 1 is then used to retain prosthetic teeth or dentures. Typical dental implant fixture dimensions are 5 mm×10 mm but considerable variation exists. Over time, the supraosseous implant surface can become colonized with a bacterial biofilm that inflames the gum tissue and often destroys the supporting bone that retains the implant which can result in the loss of the implant. Few viable treatment options exist for this problem. This bacterial mediated inflammatory process likely increases the risk for other systemic diseases such as cancer, cardiovascular disease and stroke, as has been shown in periodontitis patients.

As shown in FIG. 2, the implant site is prepared by surgically reflecting the gum 2 which exposes the jawbone 3, then drilling a hole 4 into the bone 3. The implant fixture 1 is then threaded or gently tapped into the prepared hole 4. The goal is to have the implant fixture 1 positioned such that the final biting load will be perpendicular to the jaw and that the coronal extent of the implant 1 is placed at the crest of the bone or in close proximity thereof (i.e. the entire implant fixture 1 is embedded in bone 3). The gum 2 is then sutured to close the surgical site at which point the bone grows into the implant surface undisturbed which is called "osseointegration" and usually takes about 3-6 months. Variations to this technique include: 1) implants that are self-tapping, 2) implants that are placed immediately after extraction into a fresh extraction site with a tooth replacement installed on the implant at the same visit, and 3) drilling the hole in bone directly through the gingiva without reflecting the gingiva.

After osseointegration has been attained, which is simply assumed after 3-6 months based on various research studies, the implant is surgically uncovered, unless it has been placed directly through the gingiva or in an extraction site. As shown in FIG. 3, an abutment 5 is screwed onto the exposed coronal end of the fixture 1. This abutment 5 extends from the height of the bone 3 coronally through the gingiva. The final restoration is usually a crown 6 which is either: 1) cemented or screwed onto the abutment 5 or, 2) is an integral part of the abutment 5 that is screwed onto the fixture 1. Note that there exists a portion of this implant system that is supraosseous yet subgingival, and is in contact with the gingiva. This "Transgingival Portion" (hereinafter "TGP") usually has a smooth surface to not promote bacteria or debris retention. Variations of an implant borne restoration include many implants placed into the jaw that are: 1) connected with a bar that is used to support a removable denture; 2) supporting a removable denture without a bar; and 3) connected with a bridge of crowns.

Implants can fail or become diseased for several reasons, e.g., due to microorganism colonization of the implant surfaces adjacent to the gingiva and bone, as well as iatrogenic distortion/destruction of the fixture's internal abutment attachment mechanism due to issues such as cross-threading or breakage of the abutment attachment screw.

Peri-implantitis and Peri-implant Mucositis:

As in natural teeth, the supragingival portion of the implant (which usually consists of only the restoration) will colonize with gram-positive aerobic bacteria. If this is not removed by the patient with proper oral hygiene on a daily basis, the gum tissue adjacent to the bacterial growth becomes reversibly inflamed which is known as Peri-implant Mucositis. This promotes the colonization of the subgingival implant surface with a gram-negative anaerobic bacterial biofilm. These bacteria can destroy the bone supporting the implant which is known as Peri-implantitis. Peri-implantitis prevalence rates approach 50%, depending on criteria, with 5% of all implants being lost to this disease over a 10-year period of time. The inflammation found in both of the above states is associated with increased risk of systemic diseases such as cardiovascular disease, cerebrovascular disease, and cancer.

Peri-implantitis Pathogenesis:

The pathogenesis of peri-implantitis appears to be virtually identical to periodontitis with only slight variations. As the bone around the implant is destroyed, the sintered and threaded implant surface becomes exposed to the gingival pocket and the bacteria found there. This extremely irregular implant surface is the ideal environment for the growth of the bacterial biofilms that cause peri-implantitis as it is highly bacteria retentive. It is also very difficult to arrest peri-implantitis due to the inability to access and disinfect this rough implant surface. Surgical success rates in treating peri-implantitis approach 60%, while nonsurgical treatment has been shown to be virtually ineffective. These low success rates are most likely due to: 1) the exogenous biofilm matrix which protects the bacteria, 2) the fact that the implant surface is such an ideal place for these biofilms to grow, 3) the difficulty of accessing and disinfecting these subgingival surfaces with either surgical or nonsurgical treatment, and 4) the patient's inability or difficulty in maintaining the supragingival surfaces free of bacteria.

Nonsurgical Treatment:

A nonsurgical technique to disinfect implants, as developed by Applicant, involves inspecting and debriding the subgingival portion of the implant with a periodontal endoscope while irrigating with various anti-infective chemical agents. While this technique has demonstrated an undocumented 80-90% success rate by eliminating inflammation, it is very costly and time consuming. In addition, it is not a cure. Therefore, if the patient's daily oral hygiene is inadequate (due to improper technique or access problems) then the transgingival implant surfaces will recolonize with periodontal pathogens causing recurrence of either peri-implant mucositis or peri-implantitis necessitating retreatment.

Destruction of the Implant-Abutment Connection:

The vast majority of currently placed implants possess a threaded screw hole in the coronal end that provides a means of attachment of the abutment and/or the restoration. With wear and tear, mechanical failure or operator error, these threads can become damaged which may render the implant completely unusable.

SUMMARY OF THE INVENTION

Exemplary embodiments of the present invention address at least the above problems and/or disadvantages and other disadvantages not described above. Also, the present invention is not required to overcome the disadvantages described above, and an exemplary embodiment of the present invention may not overcome any or all of the problems described above.

According to an aspect of the present invention, there is provided a dental implant to be inserted into a jawbone of a patient that includes a base segment provided at one distal end of the implant which is configured to be put inside and come in contact with the jawbone and/or regenerated/graft bone as in the case of bone grafting during a sinus-lift procedure, an attaching portion provided on an opposite end to the one distal end of the implant to which an artificial tooth is configured to be attached, and a plurality of removable segments which are configured to be put inside and come in contact with the jawbone (or regenerated/grafted bone) and are removably attached to the base segment. The segments can also be transgingival only on the coronal end, such that they do not come in contact with the bone. By providing a plurality of removable segments, if peri-implantitis were to occur, these removable segments, if infected, can be removed and either cleaned or replaced to help treat the peri-implantitis.

BRIEF DESCRIPTION OF THE DRAWINGS

These and/or other aspects of non-limiting embodiments of the present invention will become apparent and more readily appreciated from the following description of the exemplary embodiments, taken in conjunction with the accompanying drawings, in which.

DETAILED DESCRIPTION OF THE INVENTION

The following description of the illustrative, non-limiting embodiments discloses specific configurations, components, and processes. However, the embodiments are merely examples of the present invention, and thus, the specific features described below are merely used to more easily describe such embodiments and to provide an overall understanding of the present invention. Accordingly, one skilled in the art will readily recognize that the present invention is not limited to the specific embodiments described below. Furthermore, the descriptions of various configurations, components, and processes of the embodiments that would have been known to one skilled in the art are omitted for the sake of clarity and brevity.

Figure 1:
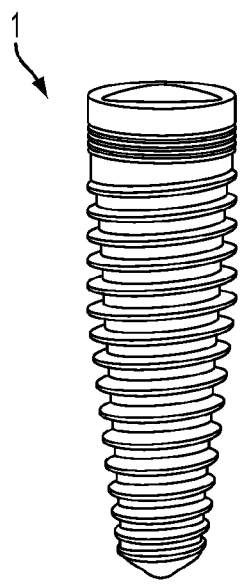
FIG. 1 is a drawing of a conventional implant that has been threaded and sintered.
Figure 2:
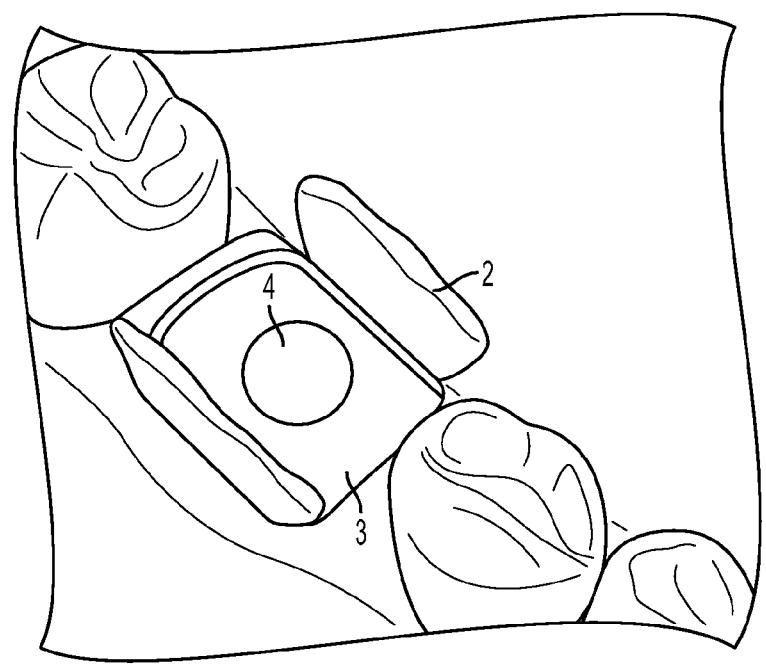
FIG. 2 is a drawing of a mouth that has been prepped for an implant with the gum being surgically reflected and an implant receptor site drilled in the bone.
Figure 3:
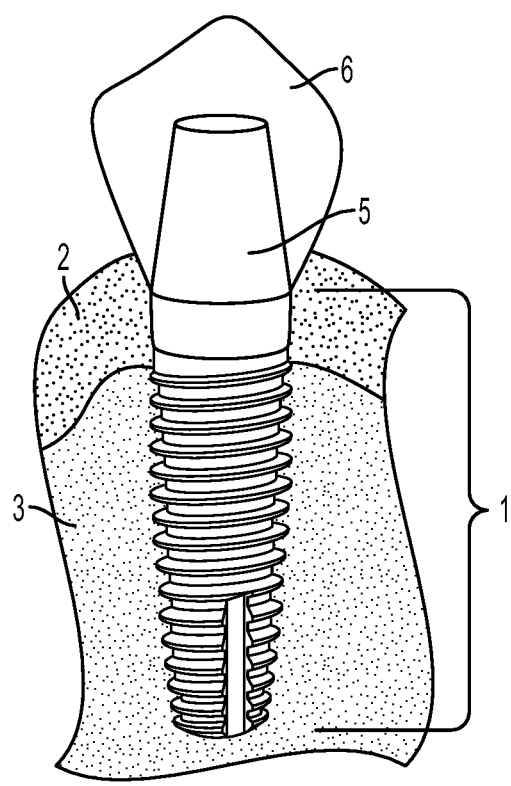
FIG. 3 is a diagram of a healthy implant.
Figure 4:
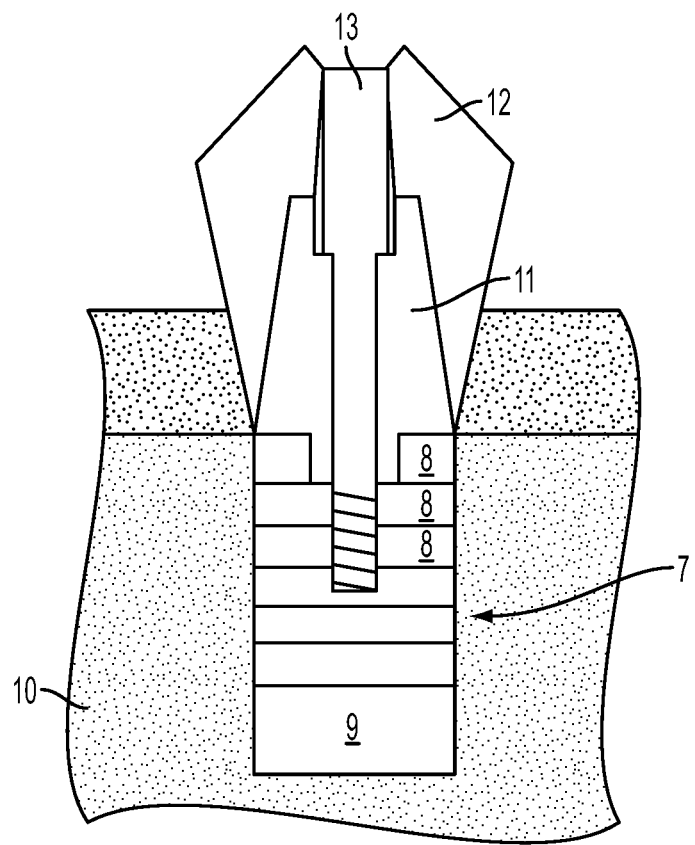
FIG. 4 is a diagram of an embodiment of an implant according to the present invention.

A non-limiting embodiment of an implant fixture is shown in FIG. 4. The implant fixture 7 is segmented to include segment sections 8 and a base 9. Also, an abutment 11 is provided on the segments 8 and a final restoration or crown 12 is screwed thereto via screw 13. The base 9 or apical portion will have some minimal length (at some minimal length of intraosseous retention there is no point to segment it further as the implant would be nonretentive in bone 10). This minimal length is about 3 mm. The segments 8 coronal to the base 9 will vary in length from 1 mm to 15 mm. The segments 8 can be straight or tapered, threaded or unthreaded, on their exterior surface.

FIG. 4 depicts the implant fixture 7 in a healthy environment. Only the abutment 11 is removable at this stage since all segments 8 of the fixture 7 are embedded in bone 10.

Figure 5:
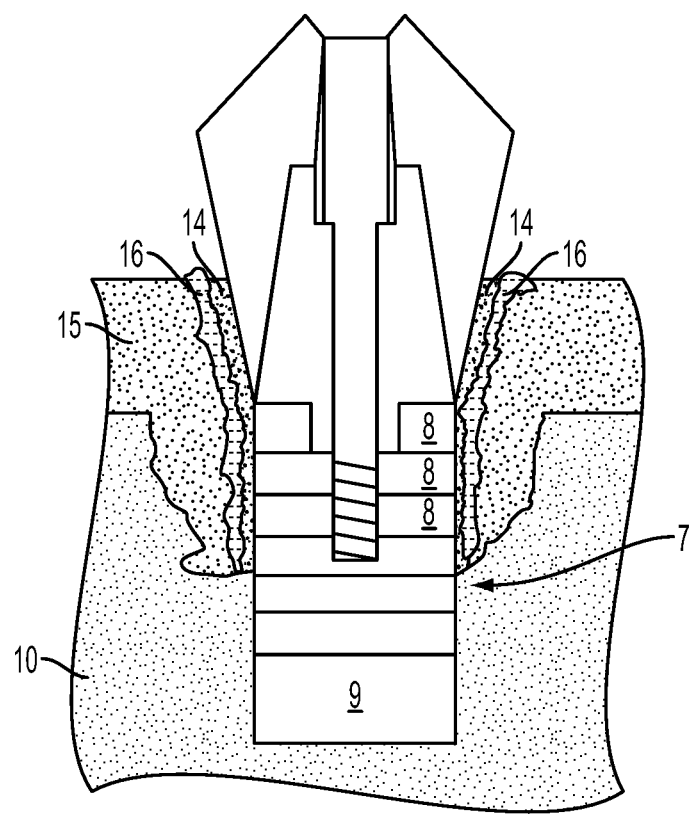
FIG. 5 is a diagram of the embodiment of the present invention shown in FIG. 4 in which infection exists and bone destruction has occurred.

FIG. 5 depicts an implant fixture 7 that has become infected by a bacterial biofilm 14 and exhibits active bone destruction (pretreatment stage). As shown, the gum 15 has inflamed gum tissue 16 as well. Due to the segment configuration of the implant fixture 7, the supraosseous portion (the "Transgingival Portion" or "TGP") can be easily disassembled and removed by the clinician at any level, in vivo, including any segments 8 of the implant that were osseointegrated at one time, but that are now supraosseous (or no longer in the bone) due to the bone destruction. Thus, upon diagnosis of either peri-implant mucositis or peri-implantitis, the infected TGP would be removed, and either replaced with a new, sterilized, smooth-surfaced TGP implant section (non-threaded, non-sintered) or replaced with the original infected implant section that has been cleaned and sterilized. In addition, this TGP section can be easily removed and disinfected at every dental office cleaning appointment to prevent and treat reinfection. It is likely that if this cleaning procedure were performed every 3-6 months with all implants, including those that are not yet infected, then peri-implantitis and peri-implant mucositis would be eliminated. In addition, the abutment attachment apparatus of the implant would also be removable, allowing servicing or complete replacement of this apparatus if it were damaged for any reason. Variations on this include: 1) Sections of the implant that are removable for cleaning by the patient on a daily basis; 2) TGP sections that are cleanable by the patient by internal irrigation; 3) Sections of the implant that contain anti-infective substances; and 4) Sections of the implant that promote new bone growth, facilitate osseointegration, or facilitate or support new biological attachment.

Figure 6:
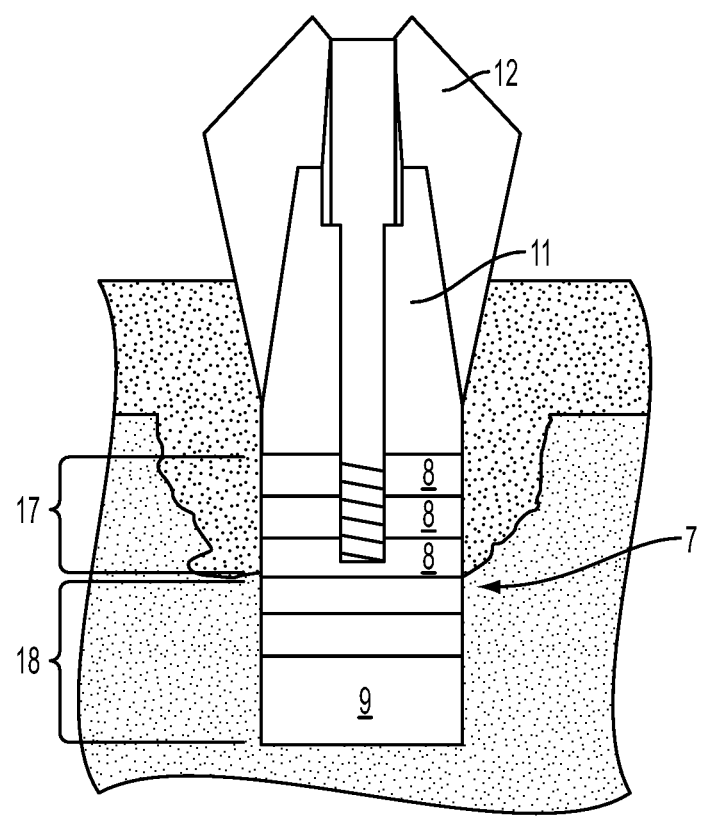
FIG. 6 is a diagram of the embodiment of the present invention shown in FIGS. 4 and 5 in which the implant has been cleaned and sterilized.

FIG. 6 depicts the implant fixture 7 post-treatment. All supraosseous components 17 including the abutment 11 and the restoration 12 have been removed, cleaned, sterilized and replaced. Note that the biofilm 14 is now gone, resulting in resolution of the inflammation which has stopped the active bone destruction. The remaining intraosseous portion 18 is retentive and stable. If it were not, then the entire implant fixture and restoration would be removed and possibly replaced with a new implant as is performed with the current technology.

Further description of the implant fixture 7 will now be made with reference to FIG. 7 (i.e., Segments on Core ("SOC") design).

The implant fixture 7 is comprised of the intraosseous base 9 fitted with an internal removable core 19 that will be retained to the base 9 by an attachment means such as screw threads 20. The core's coronal end 21 contains a means to attach the abutment 11 (see abutment 11 in FIG. 4). One or more segment sections 8 attach to the core 19 and/or the base 9, and are removable for cleaning/sterilization or replacement with sections manufactured with an altered surface (polished, bone growth promoting, etc.) if these sections become supraosseous, although these segment sections 8 are initially intended to be embedded in bone and osseointegrated.

General Method of Use of the SOC System:

1) A hole is drilled in bone (unless a fresh extraction site is used); 2) a fully assembled SOC fixture is placed in the bone; 3) clinician's option-3-6 months of unloaded healing to allow osseointegration to occur; 4) surgical uncovering (if needed) along with abutment and restoration placed; 5) if inflammation/infection occurs then restoration/abutment and all supraosseous segments would be removed, cleaned, sterilized and replaced with the segment design of clinician's choice; 5) maintenance phase begins in which all supraosseous sections are removed periodically for cleaning/sterilization/replacement if needed; 6) if at any time the clinician determines that the abutment retention attachment within the core has been compromised, the core can be removed and replaced with a serviceable core. Alternatively, various components will not require removal for maintenance cleaning if a long term anti-infective surface modification is provided on the replaced components.

Figure 7:
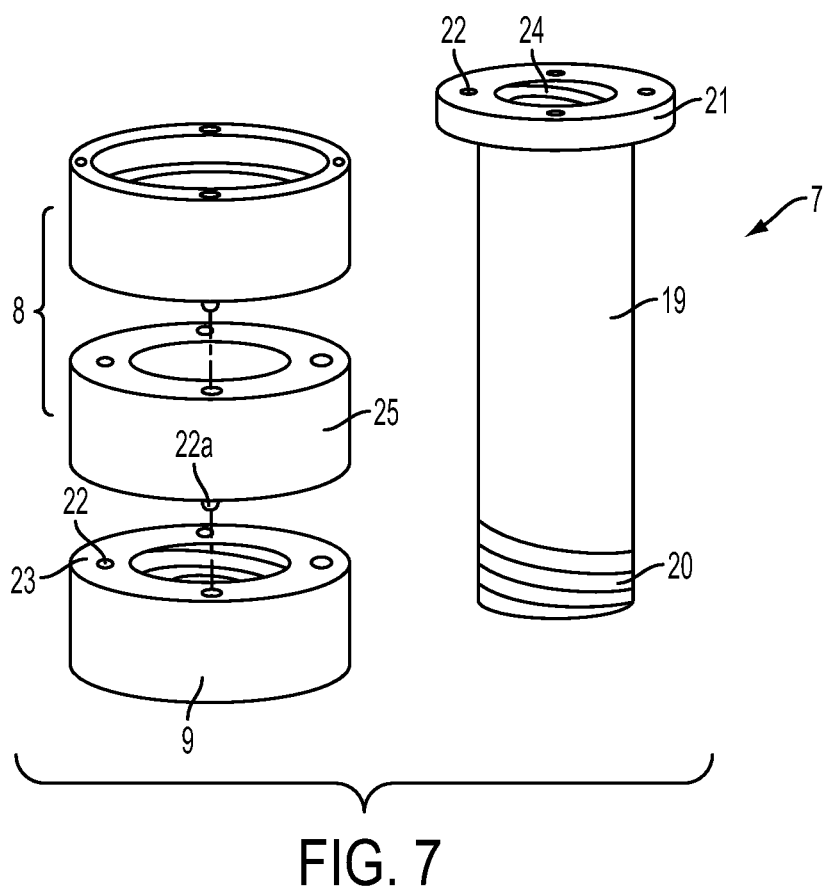
FIG. 7 is a diagram of the embodiment of the present invention.
Figure 8:
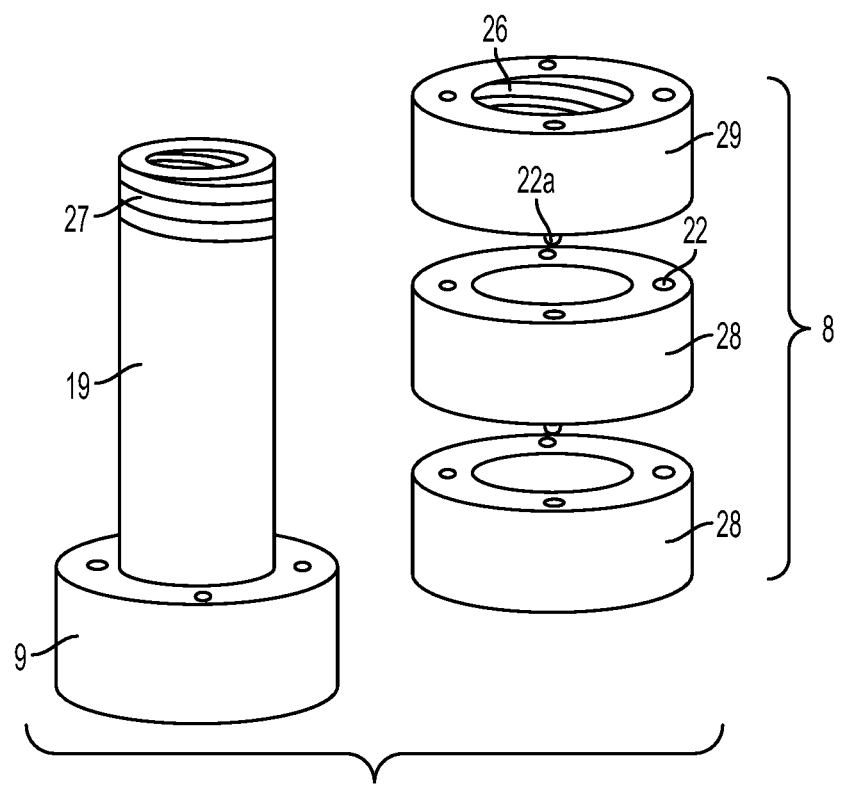
FIG. 8 is a diagram of variation of the embodiment of the present invention shown in FIG. 7.

The "Base" Segment:

The base segment 9, as shown in FIGS. 7 and 8, is of a length sufficient to provide immobile retention of the components of the implant in bone. Such length is approximately 2-5 mm, but is not necessarily limited thereto. The base 9 is internally bored out to the maximum diameter that would still maintain its rigidity and strength without deformation, as well as maintain deep but low pitch internal threads or other attachment means for the core 19. The base 9 also has several holes 22, slots, or other means, machined into its coronal surface 23 that will accept the temporary insertion of a tool for tightening (or loosening) the base into (or out of) bone during surgery, or for base removal in the event of failure of the implant. In addition, these holes or slots match corresponding pins or ridges on the mating apical surface of each segment adjacent that will provide an indexing and retention so as to prevent the segments to all act as a single unit (discussed further below). One of the benefits of this would be the prevention of rotation of a segment in relation to the segment adjacent to it. These holes and pins/ridges are optional. Furthermore, the coronal surface 23 of the base 9 is machined smooth so that subsequently attached segments will mate with a flush surface to prevent a niche for bacterial growth.

The Core:

The single-piece unsegmented core 19 is designed and configured to fit/thread/attach precisely into the base 9. If an external non-threaded core design is used (FIG. 8) then the core 19 has the option of having external "keys" (or slots) (not shown) to restrict the movement of segments 28, 29 that fit over the core provided that the segments are also keyed (or slotted) to match the core. In the FIG. 7 version, the apical portion of the core 19 and the internal aspect of the base 9 will be the mutual mating surface of these two components and may be treated or milled in such a way as to increase the retention of the core 19 when it is fully threaded into the base 9. In the FIG. 8 version, the coronal portion of the core 19 and the internal aspect of the coronal-most threaded segment 29 will be the mutual mating surface of these two components and may be treated or milled in such a way as to increase the retention of the core 19 when it is fully threaded in the threaded segment 29. The core 19 is available in various lengths. At a minimum, the core 19 is the same length as the base 9. At a maximum, the core 19 is available in the maximum standard length of a dental implant (e.g., 15 mm). In the FIG. 7 version, the coronal section of the core 19 can have similar slotting or holes 22 to allow the temporary insertion of a tightening/loosening tool which would be similar to the tool shown in FIG. 21. In the same manner, in the FIG. 8 version, the internal threaded coronal-most segment would be placed/tightened and untightened/removed with the tool shown in FIG. 21. The core 19 also has an internal concentric threaded hole 24 (or other abutment attachment means) open on the coronal aspect of the core 19, designed and configured to accept either standard or proprietary screws 13 (see FIG. 4) or other abutment attachment means.

The Segment:

Segment sections 8, as shown in FIGS. 7 and 8, of various shapes, sizes and configurations are available to the clinician, but all are placed concentrically on the core 19. The first segment 25 that will be placed will necessarily have an apical horizontal cross-section with outside diameter that matches the outside diameter of the coronal cross-section of the base 9. The segments 8 may be tapered (see TGP Segment System below) or straight, and may also be sintered or polished smooth. The segments 8 can also be threaded on the exterior surface to engage bone, similar to current technology. Details and variations of the various segment designs include:

Segment Retention Variations:

With regard to FIG. 8, the segment retention variations include: (i) A thread 26 (or other attachment means) on the internal aspect of the segment 29 that matches and engages a corresponding thread 27 on the core's 19 external aspect such that all segments are attached or threaded to the core 19, (ii) unthreaded segments 28 that fit/slide precisely over the core 19 and are held in place by the segment 29, which is a "Retentive Coronal Segment Section" ("RCSS") such that the unthreaded segments 28 are non-retentive longitudinally to the core 19 but are retained by this final RCSS 29 that is attachable (by threads 26 or other means) for retention on the core's 19 coronal end. The RCSS 29 is the most coronal segment and holds all the underlying segments 28 in place, and (iii) system in which each segment is attached to the segment underlying it by use of the holes 22 on the coronal surface of each segment 28 and a corresponding protrusion 22a provided on the bottom surface of each adjacent segment. This system of holes and matching protrusions can also be designed to serve as an anti-rotation mechanism such that each segment is precisely indexed rotationally to each adjacent segment.

Figure 9:
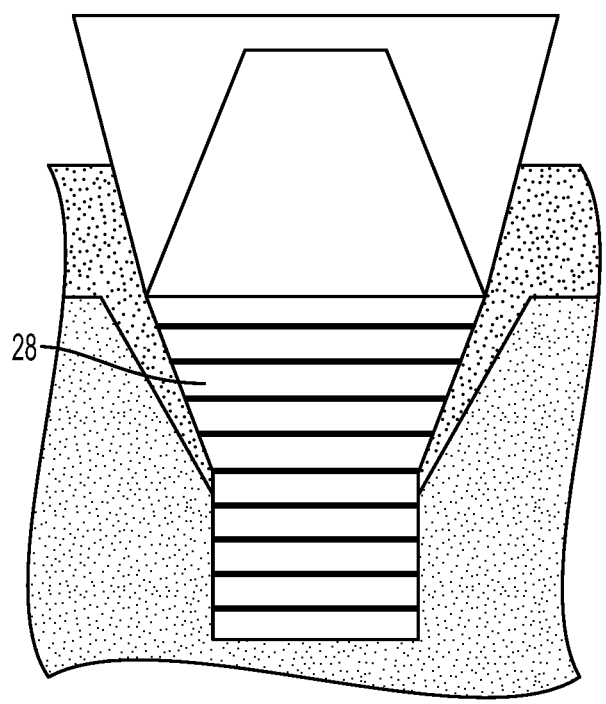
FIG. 9 is a diagram of an embodiment of the present invention in which the segments are tapered.

Segments of Variable Length:

The various segments 28 will be of highly variable length with 1 mm (or possibly less) increments, as no two applications will be identical. The purpose of this is that in some applications only a short length of segment will be required to be removed and replaced in the event of implant infection. A portion of the segments 28 may also be tapered as shown in FIG. 9. Such a system of externally tapered segments would be an option as the tooth cross-sectional area is usually larger than the implant fixture cross-sectional area. It is more ideal to have a gradual transition from implant fixture to tooth replacement as rapid transitions in cross-sectional area create steps and undercuts that are bacterially retentive and uncleanable by both the clinician and patient, therefore various tapers for different TGP sections would be made available.

Figure 15:
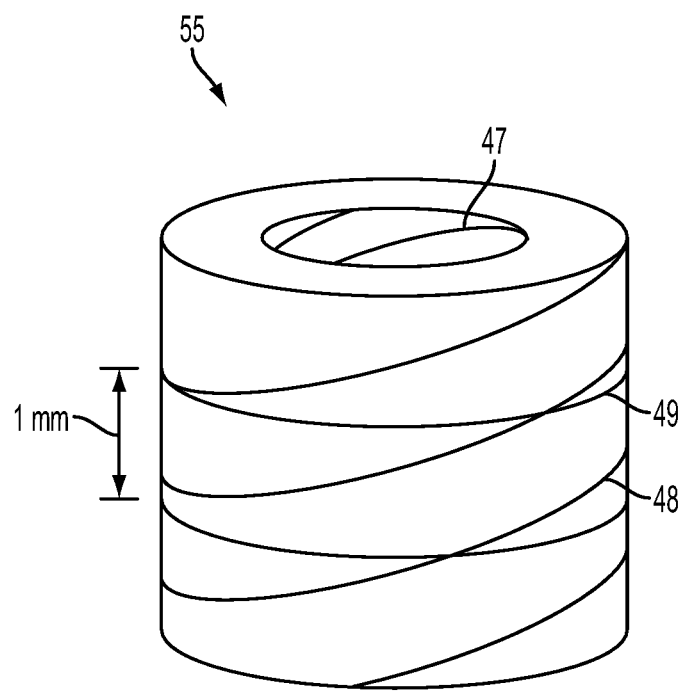
FIG. 15 depicts an embodiment of a variable length segment.

Variable Length Segment Section ("VLSS") (see FIG. 15): The VLSS 55 is a segment that is modifiable in length by the clinician. The first problem that arises with the VLSS 55 is that the clinician will not normally have the necessary machine tools to cut the VLSS 55 without disrupting the internal thread 47 and external thread 48 of the VLSS 55. Thus, using standard tools, the threads or other attachment means would become unusable due to burs and other types of deformation by imprecise cutting. The solution to this is to cut ~0.5 mm depth circumferential slots 49 into the internal and external surface of the VLSS 55, through the threads, that are ~1 mm spacing along the long axis of the VLSS 55. Therefore, a 10 mm length VLSS 55 will have nine circumferential cuts spaced 1 mm apart. These circumferential slots 49 cut into the internal and external surface of the VLSS 55 will only be required where there are threads that could be disrupted by imprecise cutting by the clinician to shorten the length of the VLSS 55; i.e. the apical 3 mm of the implant fixture will not require these circumferential cuts as the fixture would be non-retentive if less than 3 mm of fixture length were embedded in bone.

Figure 16:
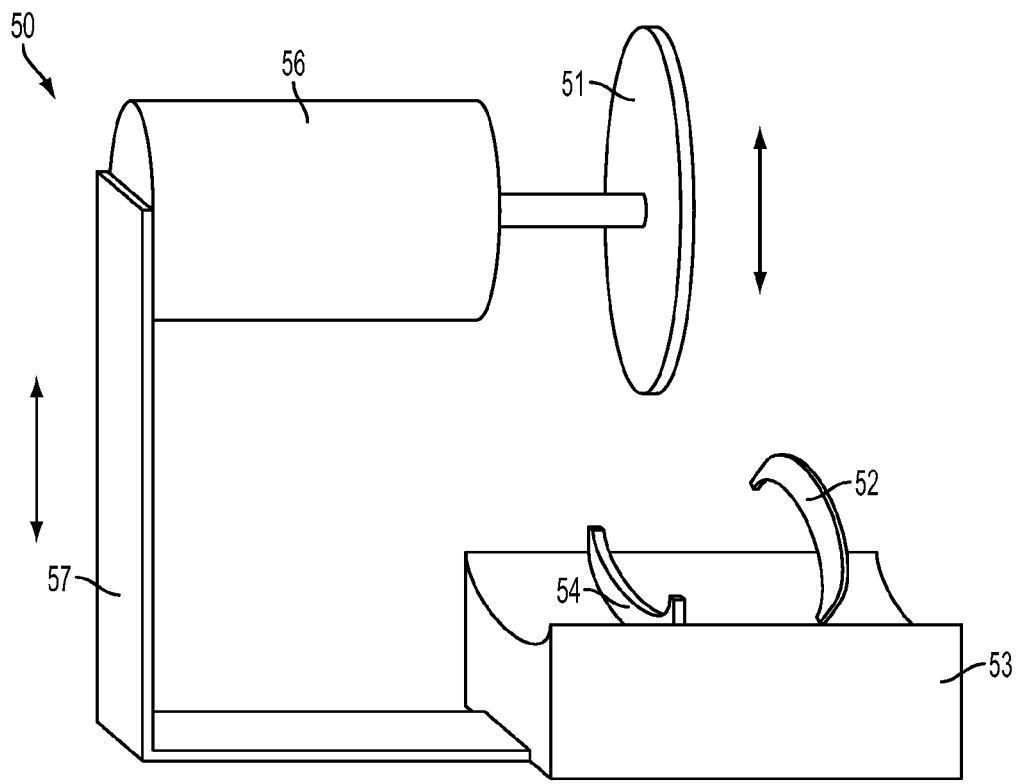
FIG. 16 depicts an embodiment of a variable length segment cutting tool.
Figure 17:
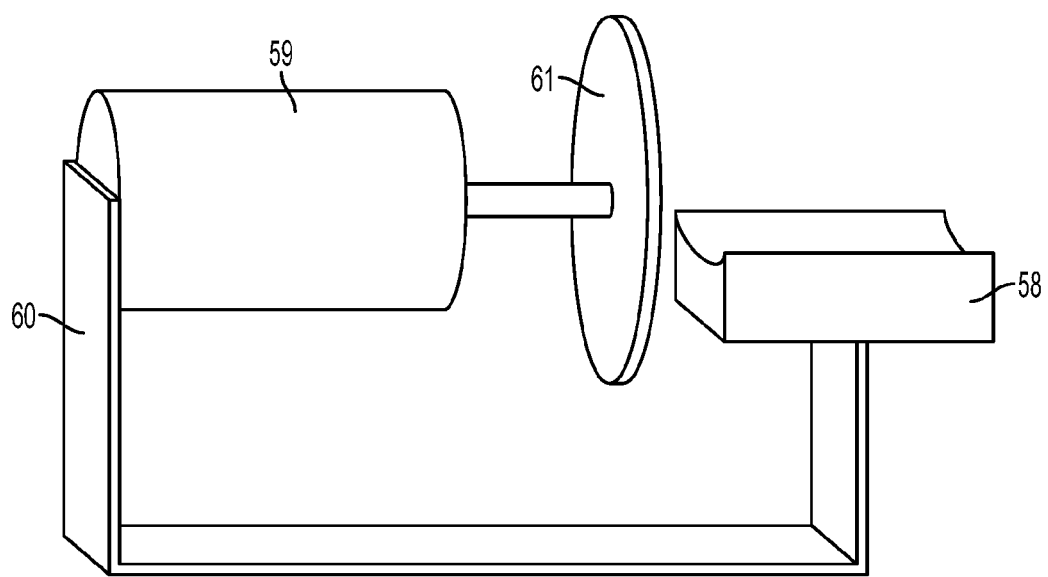
FIG. 17 depicts an embodiment of a variable length segment polishing tool.

Another problem with cutting the VLSS 55 is that if the VLSS 55 were cut with existing dental office tools, the resultant cut surface would be irregular and not provide a uniform, flush fit when mated against an adjacent segment. This non-uniform junction between adjacent segments would necessarily have gaps that are very conducive to biofilm formation and must be eliminated. This issue is addressed by the creation of a VLSS Cutting Tool ("VCT") 50 (see FIG. 16) that allows a VLSS 55 to be cut precisely by the clinician. The VCT 50 is a rotating disc 51 with a means to position the VLSS 55 perpendicular to the surface of the disk (like an orthodontic model trimmer). This allows cutting, trimming and polishing of the cut surface of the VLSS 55. For example, the VLSS 55 can be positioned using a clamp 52 that clamps the VLSS 55 to a fixing jig 53 and an indexing ridge 54 that engages a slot on the VLSS 55. The rotating disc 51 is operated by a motor 56. The motor 56 is provided in fixed relation with the jig 53 by support 57. However, at least a portion of the support 57 is movable in a vertical direction to move the cutting disc towards and away from the jig 53 as needed. As shown in FIG. 17, a similar structure is used with regard to polishing the VLSS 55. For example, the VLSS can be strapped to the jig 58. The jig 58 is connected to the motor 59 by the support 60 and is configured to slide towards and away from the polishing wheel 61.

Figure 18:
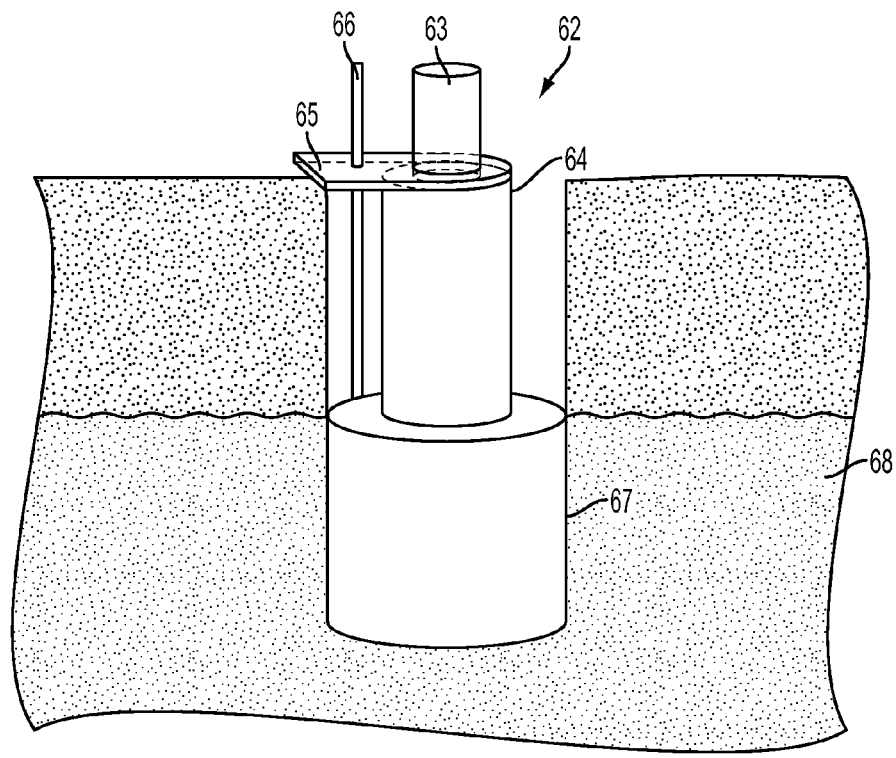
FIG. 18 depicts an embodiment of a variable length segment indexing tool.

The VCT 50 can also be used to cut the length of a core as well, but the design of the core will necessarily have to provide for "thread gaps." Continuous retention points for tightening and removal tools would be required in this cutable core design as well. Also, a VLSS Indexing Tool ("VIT") 62 (see FIG. 18) can be provided. A VIT 62 would be used to measure the length discrepancy between the core and total segment length, and then mark the exterior of the segment so that it could be placed on the VCT 50 for precise length adjustment of the VLSS 55. As shown in FIG. 18, the VIT 62 includes a bolt 63 that screws into the core 64. The bolt 63 holds the plate 65 in place precisely perpendicular to the long axis of the fixture. Then, a measuring rod 66 is used to measure the length from the coronal extent of the core 64 to the coronal extent of the segment 67 embedded in the bone 68. This measured length is used as the clinical length that the VLSS 55 will be cut down to.

Figure 19:
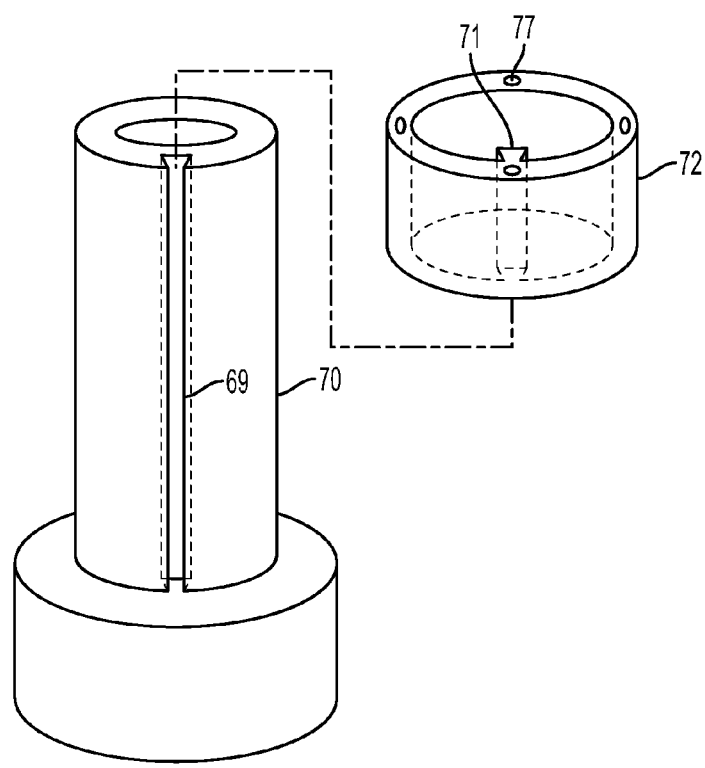
FIG. 19 depicts an embodiment of a sliding segment variation on the core.
Figure 20:
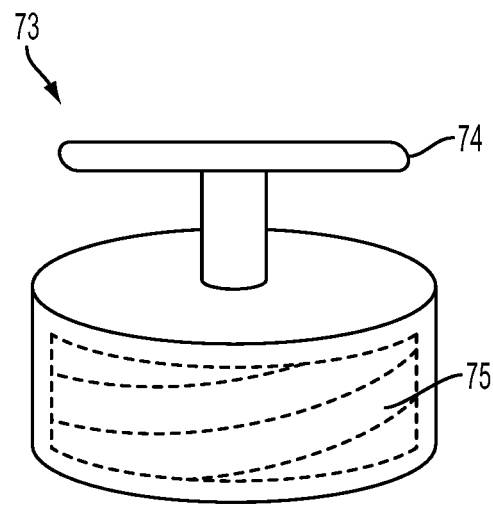
FIG. 20 depicts an embodiment of a tool for segment removal.
Figure 21:
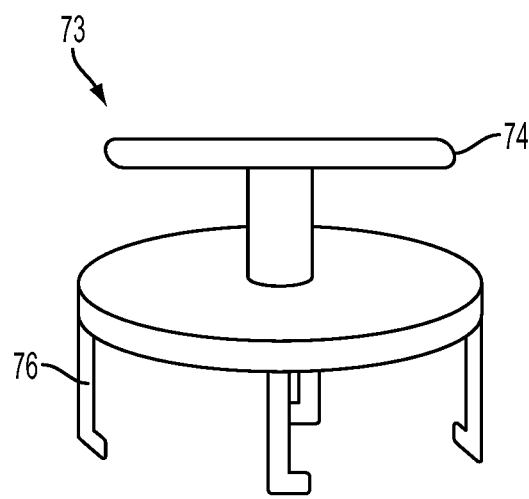
FIG. 21 depicts an alternate embodiment of a tool for segment removal.

Sliding Segment Section Variation (See FIG. 19):

In cases where the clinician requires externally threaded segment sections while still using an unthreaded core design, the core and segment sections are designed to facilitate the matching of the apical thread terminus of the segment to the coronal thread terminus of the base (or underlying segment). This design of the core would include the machining of one or more equally spaced ~0.5 width and ~0.5 depth slots (female key-ways 69) or ridges (male key-ways) running longitudinally along the entire length of the core 70. In this way, if the segment sections 72 are also "keyed" (with the opposite type of key-way or protrusion 71) to match the slots 69 or ridges, then the segments 72 slide apically over the core 70, and the external threads on the segments would align and match with the coronal terminus of the threads on the exterior aspect of the underlying section. If there is more than one key-way system, then one of the slot/ridge key-ways and its matching key on the segment, could be larger than the others to serve as a "master" or "index" key so that the segment section only has one rotational degree of freedom in how it can be placed in relation to its underlying section which would provide precise alignment and proper orientation of all external threads of each segment with its adjacent segment. These sliding segments would have some form of vertical fixation. This may be applied by the abutment being screwed into place coronally or via the RCSS design. In addition, a means can be provided to grasp the segment section 72 for removal. This could be magnetic if the segment 72 contains any magnetic material or a special tool that could be used that engages the exterior threads on the segment or to engage slots or holes on the coronal surface of the segment. For example, as shown in FIG. 20, a segment removal tool 73 is provided. The tool 73 is provided with a T-bar handle 74 and has a threaded interior 75 that fits over the exterior of a segment 72 and engages with any threads provided thereon. As shown in FIG. 21, a variation of the tool 73 has prongs 76 as opposed to the threaded interior 75 shown in FIG. 20. The prongs 76 are used to engage with slots 77 provided in the segment 72 (see FIG. 19).

Figure 26A:
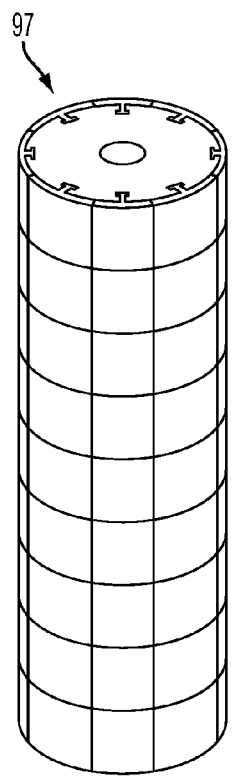
FIG. 26A depicts a puzzle box embodiment of sliding segments on a core in an assembled state.
Figure 26B:
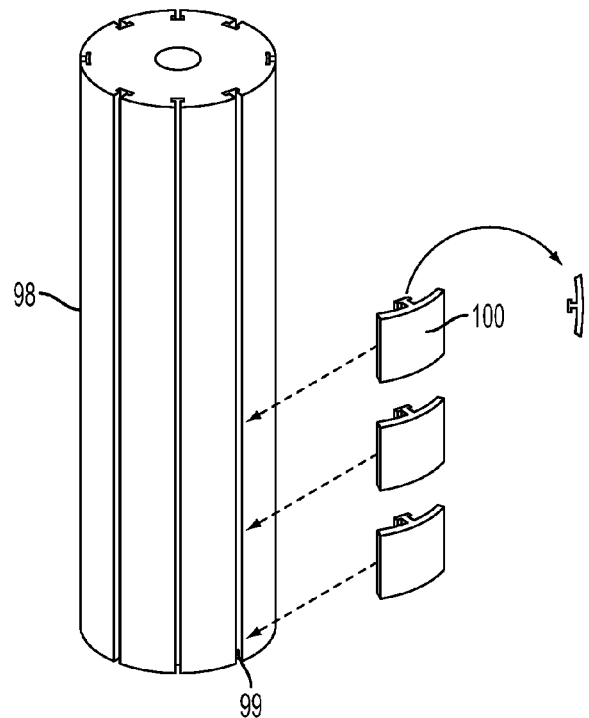
FIG. 26B depicts the puzzle box embodiment of FIG. 26A in a non-assembled state.

A variation of the sliding segment configuration discussed above is a so-called puzzle-box design 97 as shown in FIGS. 26A and 26B. FIG. 26A shows the design in a fully assembled state. As shown in FIG. 26B, the core 98 is provided with keyed slots 99 that are configured to accept the pieces 100. The pieces 100 can be designed to have a tab that slides into the keyed slots 99. Adjacent pieces 100 are configured to mate with adjacent pieces 100 with a flush joint. The exterior of the puzzle box design 97 can optionally be threaded or sintered for placement in bone. Upon discovery of infection, any supraosseous pieces 100 are removed and replaced with clean pieces or a suitable segment section of the clinician's choice.

Figure 22:
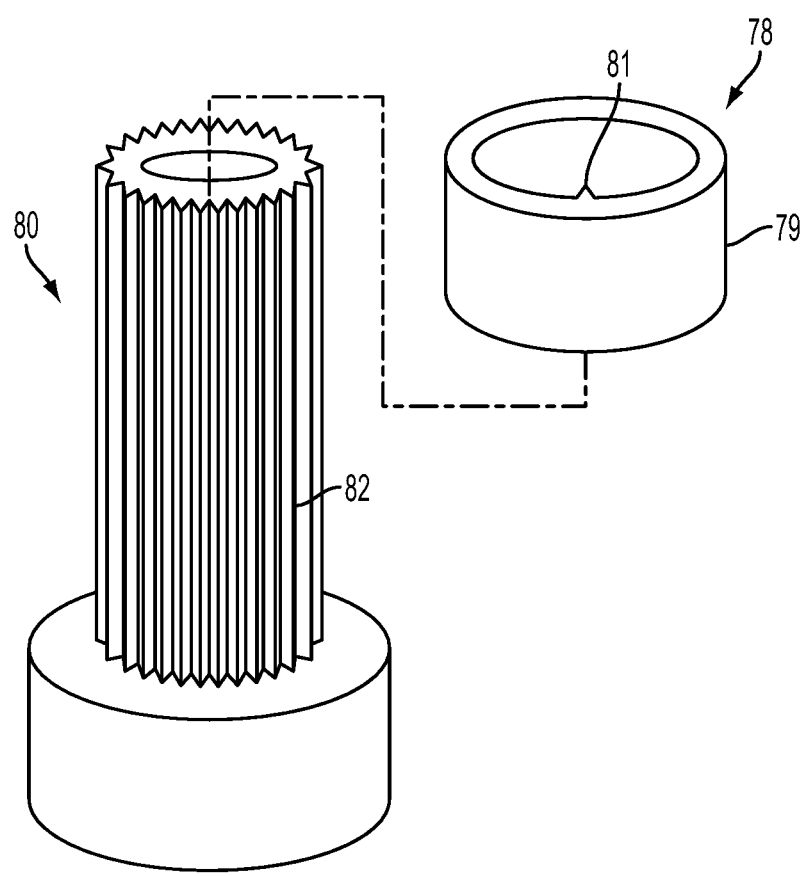
FIG. 22 depicts an embodiment of a polishable segment variation on the core.

Polishable Segment Variation (See FIG. 22):

Cases exist in which the crestal bone attachment to various segments is not circumferentially uniform. Specifically, the bone is not bound to the segments equidistant from the coronal limit of the fixture. Therefore cases will exist where the most coronal osseointegrated segment is not equally osseointegrated at all points around the external circumference of the segment. This will necessarily result in areas of the segment that may be sintered or threaded but are exposed to the pocket wall and may become contaminated with bacterial biofilm. This is highly undesirable due to the biofilm retentive nature of a non-smooth and non-polished surface. The solution to this is to have segment units available that are not keyed on the internal aspect so that they may rotate freely or to have a core 80 and matching segments 78 with multiple key-way systems. As shown in FIG. 22, the segment 78 is provided with one or more protrusions 81 that engage with the keyed surface 82 of the core 80. The segments 78 of this variation will have many degrees of freedom in the horizontal rotational orientation of this variation's segment in relation to the core with the number of degrees of freedom of rotation proportional to the number of key-ways in the system. The reason for this is that this variation's segments 78 will have a sintered surface 79 that is easily polished by the operator to address the variations of bone height available for osseointegration at the osseous crest, thus the area that is predicted by the clinician to be exposed to the pocket wall, and not osseointegrated, may be polished smooth so that part of this variation segment's external circumference will be sintered while other aspects of it will be polished.

Figure 10:
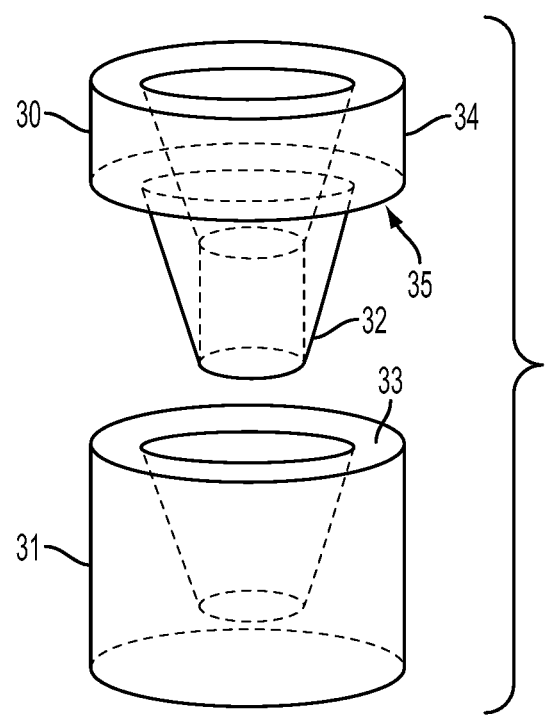
FIG. 10 is a diagram of another variation of the embodiment of the present invention shown in FIG. 7.

Coreless Fixture Design ("Nested" Version):

In the nested version, as shown in FIG. 10, a system of segments 30, 31 attach to each other in a longitudinal direction. They derive their longitudinal rigidity from their attachment to each other and not from an internal core that may or may not be used in this design. If it is used, it would contribute to the rigidity of the system but would primarily be used as a removable means to secure the abutment. The base segment 31 consists of a cylindrical parallel-walled titanium piece. Dimensions would typically be 3 mm minimum length and 3 mm minimum width. The apical aspect can be polished, sintered or open. The external aspect can be threaded, unthreaded and/or polished or sintered. The coronal aspect would be flat, polished and open. The internal aspect could be threaded and would provide for the insertion of partially threaded segments 30. These segments 30 would nest into the base segment 31 upon complete thread seating and form a virtually seamless junction when the adjacent segment 30 nests into the base segment 31.

The segments 30 would be a one-piece partially cylindrical design with two main aspects. The apical aspect 32 would be a tapered (or nontapered) threaded section that is designed and configured to precisely fit, and nest into, the open coronal portion 33 of this variation's base segment 31. The coronal portion 34 of the segment 30 would consist of a collar (polished, unpolished, sintered, unsintered, etc) with an apical surface 35 that precisely mates against the coronal portion 33 of the base segment 31. It will also precisely mate against other segments 30 placed coronally such that all segments 30 are identical and will mate/nest into each other and the base segment 31.

A variation on this design would be made to allow the construction by the clinician of a fixture that is tapered on its exterior (see, e.g., FIG. 9). This would be accomplished by having various sized tapered segments that would be placed such that the apical aspect of the one segment would have the same diameter as the coronal aspect of the segment (or base) below it. Another variation would be that the segments attach to each other via a proprietary locking mechanism.

Methods for prevention and treatment of peri-implant infection are set forth below.

Figure 23:
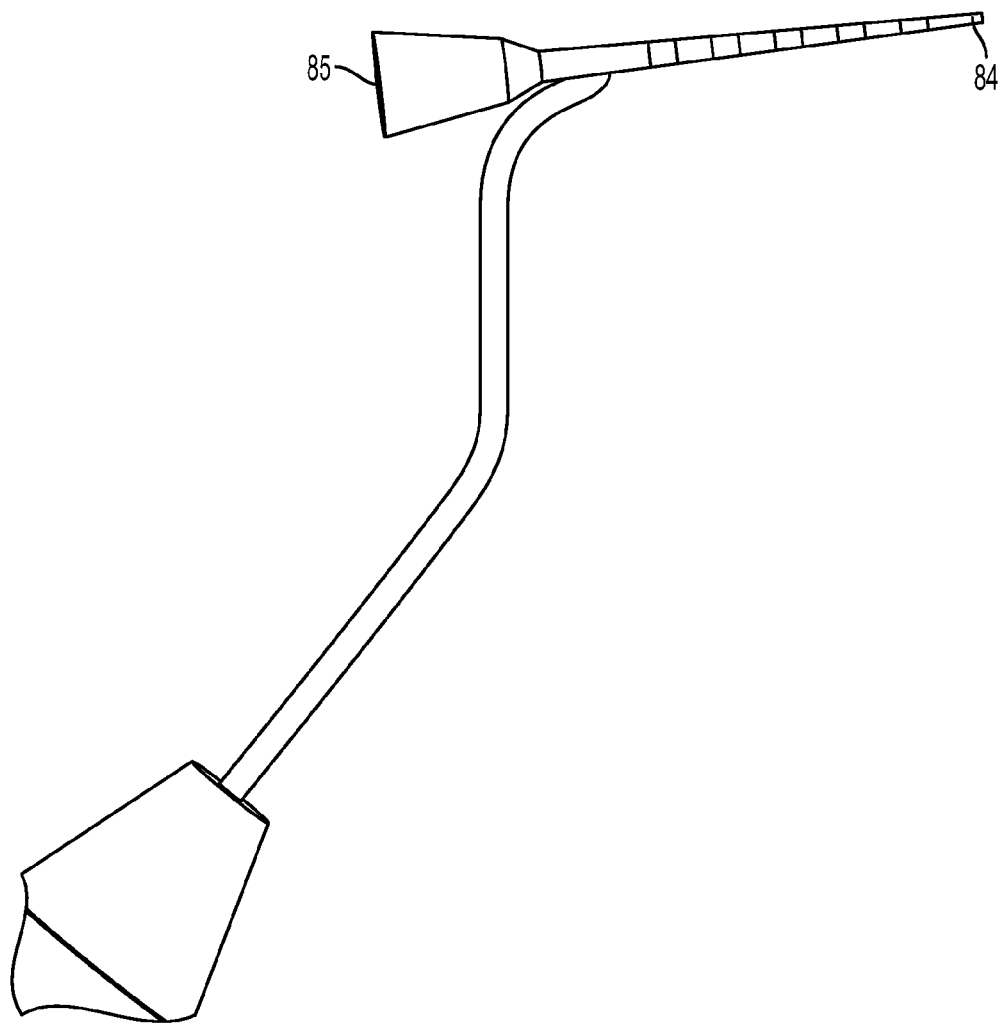
FIG. 23 depicts an embodiment of an endoscope.

Method to Accurately Polish Segment Section:

To aid in the determination of what areas require polishing, a perio-probe marked diagnostic endoscope 83 (see FIG. 23) can be used such that it is inserted into the crevice, the distal aspect 84 of the endoscope probe is put into contact with the osseous crest, then the proximal aspect 85 of the endoscope is viewed in relation to the coronal aspect of the implant. The calibrated markings on the endoscope are used to indicate the height of the osseous crest in relation to the implant at various areas around the circumference of the implant. In this way, a "map" of the areas on the segment section that will be in contact with the pocket lining of the gum can be determined. Then the segment section can be removed and polished.

Method to Address Partially Integrated Segment Section:

Cases will often present with a segment section that has various areas osseointegrated around the external circumference of the segment, while other areas of the segment would be exposed to the pocket lining of the gum and probably infected with biofilm. This necessarily results in a segment that would not be simple to remove for definitive disinfection. This issue is addressed by using a non heat generating, cooled, hollow-core end-cutting drill (powered trephine) 86 (see FIG. 24; discussed below) at very slow revolutions per minute ("RPM") to remove a very thin layer of bone around the partially osseointegrated segment section to allow for ease of removal of the segment. Once the segment is removed, it can be replaced with a sterile sintered segment section that has been polished on the pocket-exposed aspects by the clinician. In addition, the narrow space left between the intact bone and the implant by the end cutting drill 86 will provide an ideal crevice for the placement of bone grafting materials to facilitate new osseointegration of the newly replaced partially polished segment section. The bone grafting material is a bone enhancement material that can be osteoconductive, osteoinductive, osteopromoting, osseointegrating and osteogenic. Thus, any discussion of bone grafting material(s) in the specification and claims includes any one or more of the listed bone enhancement characteristics. An alternative is to simply replace the segment with a polished segment, intentionally devoid of bone grafting materials which would create an environment in which the entire TGP can be removed frequently for maintenance cleaning/sterilization.

Method to Address Failing Base:

Cases will arise in which inadequate area of osseointegration of the base exists and/or in which it is unrestorable due to damage or other factors. Current technology is inadequate in these situations as partially osseointegrated implants are usually impossible to remove without a highly invasive and destructive procedure in which large amounts of bone are removed around the implant to provide access to the implant for removal. This leaves a large osseous defect that may be impossible to regenerate, and the procedure itself may have caused collateral nerve damage or other tissue damage. This issue is addressed by designing all fixture components as follows: All base pieces 9 are configured such that a 90 degree angle is provided between a side of the base 9 and the apical aspect thereof (see, e.g., FIG. 4). If the base 9 is placed in bone 10 but requires removal after partial or full osseointegration, then the end-cutting Drill 86 (discussed below) that is designed with ports 90 for both internal and external irrigation, with an internal aspect that precisely fits the external aspect of the base 9 is used. Inspection of the existing base 9 will determine the length of the drill 86 to use. The drill 86 is placed over the base 9 and slow RPM with copious irrigation from all ports is performed until maximum depth is reached (as the drill matches the base 9 and attached segments 8 in length). At that point, a fixture insertion tool is used to twist the implant which will easily break loose any osseointegrated attachment to the polished apical extent of the base 9. To facilitate removal, the apical surface of the base can be manufactured of a nonosseointegrating material (e.g., stainless steel) with a surface prepared to be non retentive (e.g., polished). With the precise nature of the bone removal in this situation, a predetermined size and shape to the osseous walls of this defect will have been created by the drill. This will allow for the insertion and firm retention of a slightly oversized implant (should be segmented also) that is designed and configured for optimum osseointegration into this new site.

End Cutting Drill with Optional Indexing Tool (See FIG. 24):

a sterile, surgical, specially designed thin-walled, hollow, end-cutting drill (trephine type drill) that is designed with ports 90 for both internal and external irrigation, and lubrication, with an internal aspect that precisely fits the external aspect of all components of the fixture (base and segment sections). Additional features of this drill include a sharp cutting shield 88 at the distal extent of the drill 86 (to allow use without surgical reflection of the gum tissue) as well as a highly polished external surface of the drill and cutting shield 88 to decrease tissue drag and friction during use. Inspection of the existing fixture will determine the length of drill to use, but the drill would be available in diameters such that the inner diameter of the drill matches the outer diameter of the implant. The internal length of drills available will precisely match the length of all cores and possible combinations of base+segments available such that for any given fixture, a drill will be available to remove a thin layer of bone surrounding the fixture precisely to its apical extent, providing for easy removal of the implant fixture. In addition, shorter lengths of the drill will be available to match any combination of segment sections that might need to be removed (i.e. internal length of 2 mm, 4 mm, 6 mm, etc), such that the drill can be used as a depth guide providing the operator with definitive confidence that pressing the drill to its maximum length will remove bone around only the segment sections calculated to be removed (whether it be one, two or all segment sections from the base). The drill is always operated with slow (5-20) RPM with copious irrigation from all ports until maximum depth is reached (as the drill matches the fixture in length).

Figure 24:
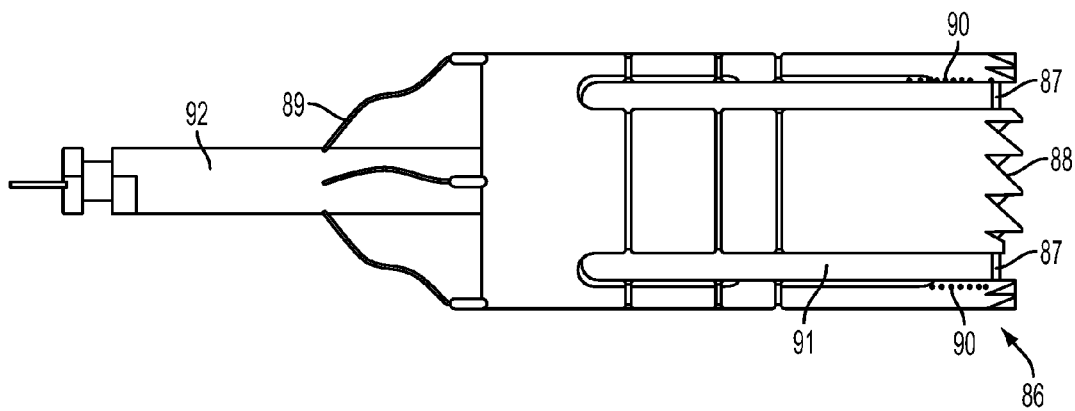
FIG. 24 depicts an embodiment of an end cutting trephine drill.

With further regard to FIG. 24, the end cutting drill 86 is provided with thin stabilizing strips 87 between the portions of the cutting shield 88 to prevent distortion of the end of the drill 86 under load. Also, water is input to the drill 86 and travels through the water channels 89 to ports 90 provided in the cutting shield 88. Due to the configuration, water is capable of flowing up and out of the surgical site through the open channels 91. Furthermore, the drill support rod 92 can be made hollow to accommodate the apical portion of the indexing tool 93 discussed below. Such fit assists in guiding and aligning the drill 86 over the implant.

Figure 25:
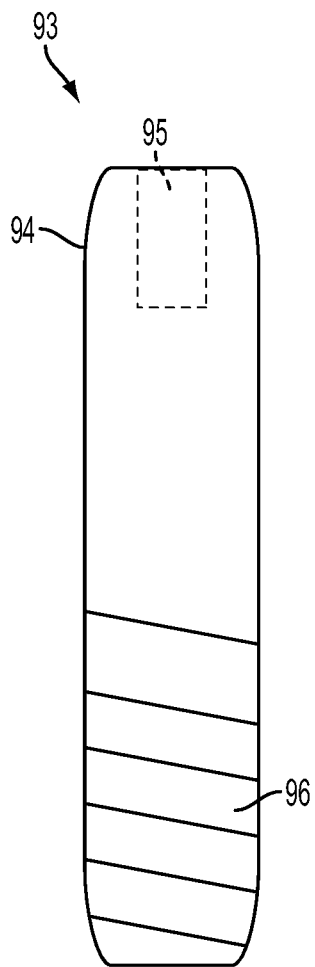
FIG. 25 depicts an embodiment of an indexing tool to be used with the end cutting trephine drill of FIG. 24.

Indexing Tool (I) (See FIG. 25):

Due to the precise fit of the drill 86 on the fixture, clinicians may have difficulty indexing and aligning the drill 86 on the fixture. In these cases an indexing tool 93 will be secured in the place of the abutment. It will be sized and configured to facilitate placement and alignment of the drill 86 on the fixture, substantially 3 mm or more in length, diameter like the fixture or of a diameter to fit into a recess/channel within the drill support rod, but in both cases with a slight taper 94 at the coronal-most section for ease of placing the internal aspect of the drill 86 over the indexing tool. In the case of the indexing tool with diameter of the fixture, the drill will require an internal length to not only match the length of the fixture as required but would necessarily need to incorporate the extra length of the indexing tool. As shown in FIG. 25, the indexing tool 93 is provided with a hole 95 for using a wrench to tighten the indexing tool 93 into the fixture. Also, threads 96 allow for a precise fit of the indexing tool 93 into the abutment hole of the fixture.

General Example of Method of Use of Drill:

In partial osseointegration and/or infection of segment sections (with resultant bone destruction and partial loss of osseointegration), cases will arise in which segment sections have various amounts of surface area that are osseointegrated while other areas are exposed to the pocket wall and prone to infection. There are two ways to treat this: 1) When there is only slight (1 mm+/−) non-osseointegrated surface of the coronal segment section and the clinician is not certain that the non-osseointegrated section is infected, then a periodontal endoscope can be used to access the pocket-wall exposed segment section surface and can thoroughly debride and disinfect it with irrigants, oxidizing agents, and/or other anti-infective agents. Segment sections coronal to the apical-most partially integrated section can be replaced with smooth, sterile stainless steel segment sections which should cure the infection and can be maintained without infection by frequent removal, sterilization and replacement (or coating/treating the surface with anti-biofilm materials). 2) If large areas of segment section(s) are non-integrated and/or infected, but still not removable due to partial osseointegration, then the clinician would remove the small amount of remaining bone retaining any segments using the drill 86. Thus any partially integrated segment section(s) would then be removed.

At this point, two cases are possible: (1) if the clinician concludes that bone architecture is amenable to osseointegration of a new segment section, then a new, sterile, titanium, sintered-surface 1 mm (or more) height segment section could be placed with bone grafting material. A sterile smooth-surface stainless steel segment section (or sections) would then be placed coronal to or on top of this new sintered segment section in zones of the pocket lining that are not deemed by the clinician to have any potential for osseointegration. Bone would integrate with the new sintered segment section and pocket inflammation would resolve along the nonsintered stainless steel segment section. (2) If the clinician concludes that bone architecture is not amenable to osseointegration of a new segment section, then only a new, sterile, smooth-surfaced stainless steel segment section would be secured in place and pocket inflammation would resolve along the stainless steel segment section.

In both cases (1) and (2) above the nonosseointegrated segment sections would be removed every 3 months (+/−) for ultrasonic debridement and sterilization, followed by immediate replacement, thus curing the implant infection and maintaining the area in a state of clinically insignificant bacterial load, unless the removable segments are coated/treated with a anti-biofilm material in which case the segments would need to be removed less frequently for cleaning and possible recoating with anti-biofilm material.

Sintered TGP Segments:

The most apical TGP segments that are removable due to bone destruction may be replaced with sterilized, sintered segments which may promote osseointegration of the new, sterile, sintered segment as discussed above. The method involves a clinician diagnosing peri-implantitis around an implant. The clinician removes the crown and all the segments down to the osseous crest. If it is deemed that bone regrowth can occur at the implant site, sintered TGP segments of a length that bone regrowth will occur are placed. Alternatively, several sintered TGP segments can be placed and, at a later date, the most coronal sintered TGP segments that do not osseointegrate can be removed. Polished TGP segments are then placed on top of, or coronal to, the sintered TGP segments if there is available space. Then, the abutment and crown are replaced. The patient is instructed in appropriate oral hygiene and the crown, abutment and polished segments will be removed every 3 months for professional cleaning if required. After a period of time has elapsed in which it is judged that the maximal amount of bone growth into the sintered TGP segments has occurred, the crown is removed along with the abutment and all segments that have not osseointegrated. Finally, sterile polished TGP segments are placed on top of or coronal to the most coronal osseointegrated sintered TGP segment as a long term solution. Periodic removal and cleaning (and/or sterilization) for all removable segments is recommended as a maintenance procedure depending on the type of coating or surface treatment of the TGP segments.

Segments Treated to Cause and/or Support Tissue Growth and Attachment:

Special apical segments with bone grafting material, biocompatible and/or anti-biofilm coating material, applied by the manufacturer, to the external aspect of the segment may be designed and placed to promote and support the growth and attachment of bone, connective tissue and epithelium, and/or prevent the growth of bacterial/fungal biofilms. The method of treatment and placement would be analogous to the method set forth above. A combination of the bone grafting material and materials that promote connective tissue growth, biocompatibility, epithelial down-growth inhibition, and materials that promote cementum formation are hereinafter collectively referred to as tissue growth management material. Thus, the term "tissue growth management material" may include any material or surface treatment that exhibits one or more of the above characteristics including those of bone grafting material as previously described above.

Figure 11:
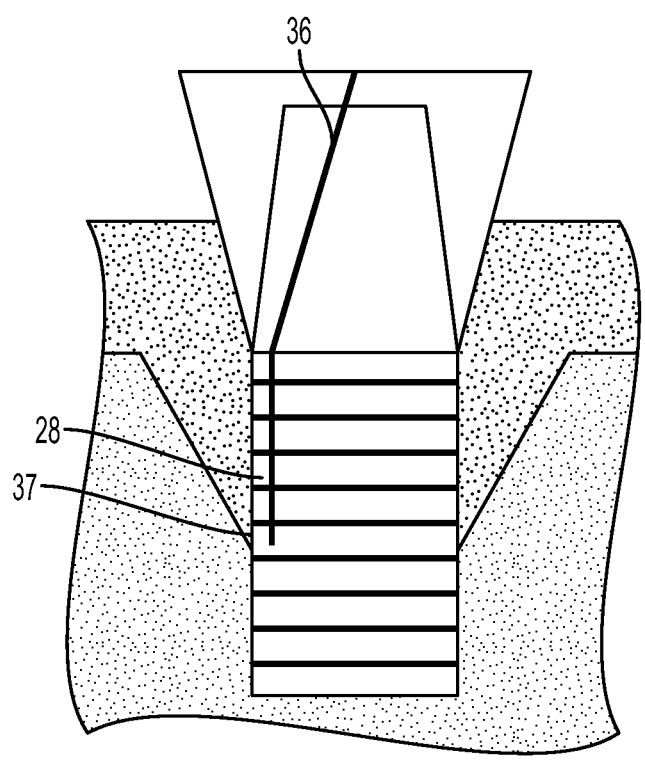
FIG. 11 is a diagram of an embodiment of the present invention in which internal channels are formed that allow the introduction of antibacterial substances.

Flushable TGP:

As shown in FIG. 11, a TGP system can be provided with internal channels 36 that will conduct fluid from an external supragingival port, through the abutment and supraosseous segment sections, to exit through ports distributed evenly at the most apical but supraosseous segment sections 37 that will allow introduction of fluid/gel antibacterial substances by the patient and clinician such that the most apical extent of the gingival pocket can be flushed on a daily basis and at professional maintenance appointments.

Flushable Abutment:

An abutment (similar to the Flushable TGP) that has irrigation entrance ports on the occlusal aspect of the crown allowing for irrigant to be transmitted through the body of the abutment to irrigant exit ports at the base of the abutment to provide irrigation at the base of a gingival pocket when the coronal extent of the implant fixture is positioned at the osseous crest (i.e. ideal implant placement with no bone loss). Method: The clinician determines that a newly placed implant is at high risk for infection. The clinician therefore places the flushable abutment at the time of first loading of the implant and instructs the patient to irrigate the gingival crevice on a daily basis through the abutment ports with the appropriate antibacterial fluid/gel to prevent infection of the subgingival portion of the implant. As an alternative to having ports at the apical extent of the crevice, ports may be distributed throughout the TGP portion. In addition, an internal sleeve may be used to selectively block various areas of the ports to prevent irrigation in areas of integration as well as prevent ingrowth of tissue.

Figure 12:
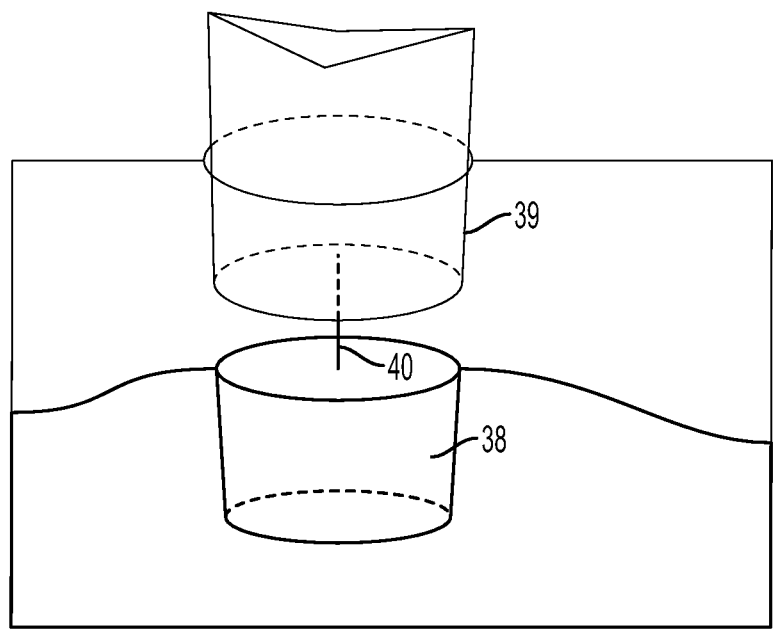
FIG. 12 is a diagram of an embodiment of the present invention in which the patient can remove the prosthesis for hygiene.

Single-Tooth Patient Removable TGP:

A restorative system for single-tooth restorations in which 90% to 100% of the TGP is actually attached to the removable prosthesis (crown) such that the patient can remove the prosthesis for hygiene which would also remove the TGP, leaving only the intraosseous portion of the implant in place. As shown in FIG. 12, retention is accomplished by various means including: 1) a very short magnetic abutment (1 mm thickness) screw-attached to the fixture 38, with the opposing magnet attached to the removable TGP 39 on the prosthesis. This would be indexed with a pin 40 (or other indexing means) on the fixture side and a hole on the removable TGP side or vice-versa, or 2) an elastic segment on the retention pin that would "snap" into a matching recess within the pin indexing hole on the TGP.

Figure 13:
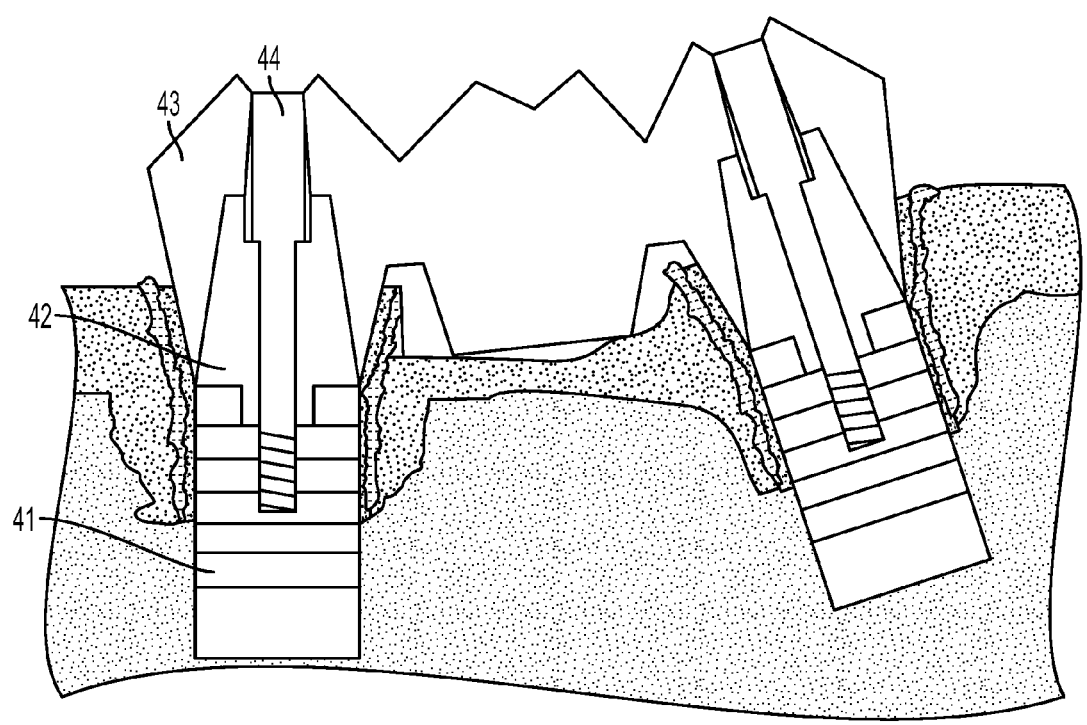
FIG. 13 is a diagram of an embodiment of the present invention in which the bridge/abutment unit can be removed.

Multi-Tooth Removable TGP:

In the case of a "bridge" where at least two tooth restorations are attached to each other (side by side), a different abutment system will be required to allow both units to "draw" away from their fixtures simultaneously without binding into undercuts which would prevent removal. This issue is addressed by providing the abutments for both fixtures with flush mating surfaces with their respective fixture (See FIG. 13). Therefore both the fixture 41 and the abutment 42 will require flush mating surfaces. The abutment 42 will be retained with its respective tooth restoration 43 with a screw 44 sized and configured to retain the abutment to its respective fixture 41.

Figure 14:
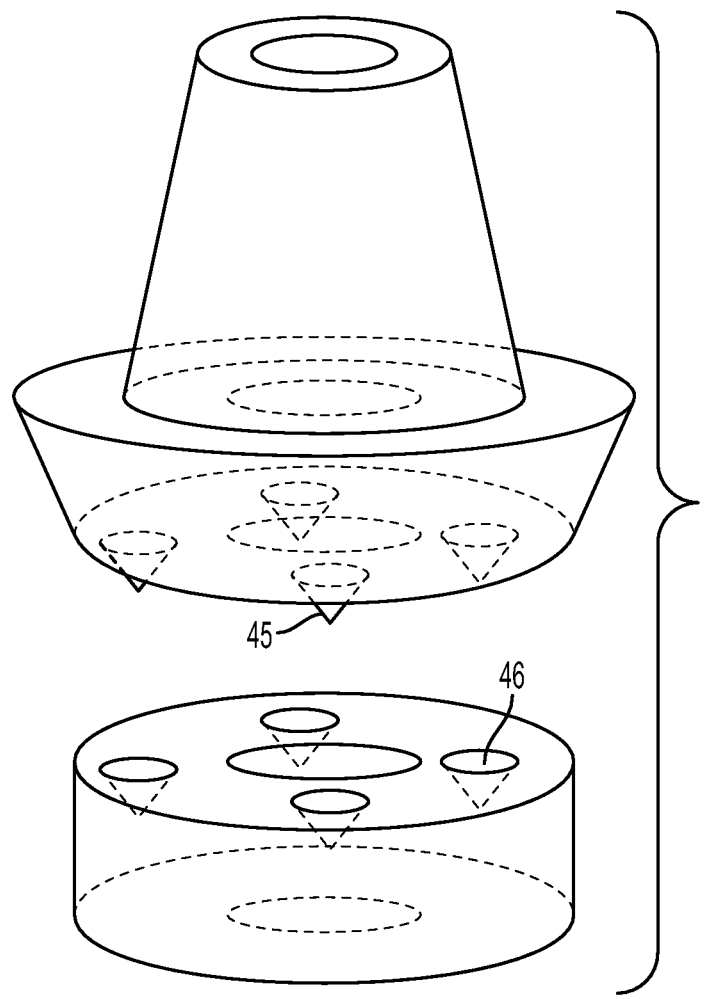
FIG. 14 is a diagram which shows in detail a bridge abutment and indexed mating segment that allows removal of an intact bridge from its underlying implant fixtures.

An "Indexing Feature" could be used in the system described above to assist in preventing rotation of the abutments and aid in retention and stability of the abutment and restoration. As shown in FIG. 14, one possible embodiment of this indexing feature would consist of one or more "male" cone-shape projections 45 on the abutment mating surface that would fit precisely into location and sized-matched female cone-shaped recesses 46 on the mating segment surface. Alternatively, the projections 45 can be formed on the mating segment surface with the recesses 46 formed on the abutment mating surface. The angulation of the congruent walls of the indexing feature, with respect to the horizontal surface of the mating segment, is important as follows: (a) If the walls of the indexing feature are made almost parallel, these walls would interfere with the "draw" and removal of the abutment from the mating segment although the more parallel they are, the more retentive they are, (b) if the walls of the indexing feature are made less parallel, these walls would not interfere with the "draw" and removal of the abutment from the mating segment, but these walls would be less retentive as well which is a disadvantage, and (c) the conclusion is that there will be an ideal angulation of these walls that does not interfere with "draw" but that does provide adequate retention of the abutment to the mating segment. The system may require different angulations in this regard to be available to the clinician.

Electrostimulative TGP (not Shown):

The various segments of the segmented implant would be removable and replaceable with segments that act as either insulators, cathodes or anodes with a power source mountable either external to the implant or internal to the implant. The method using such segments includes: 1) clinician diagnoses peri-implant disease; 2) all supraosseous portions of the existing segmented implant are removed; 3) insulator, anode or cathode segments are attached to the intraosseous portion of the existing implant in any combination or configuration; 4) the existing intraosseous portion of the implant can be used as an anode or cathode if necessary; 5) electric current or an electromagnetic field is applied to the anode and cathode; 6) the power source is installed and activated; 7) the prosthetic tooth replacement is installed; 8) patient leaves the office and returns periodically for power source replacement and follow-up to evaluate bone growth; 9) upon satisfactory bone healing the segments can be left in place or replaced with a TGP of the clinicians choosing.

UV Segment and UV Abutment:

This embodiment utilizes segments and an abutment constructed of a UV (or other wavelength) transparent material. This segment/abutment will have a recess in its center to place, either permanently or temporarily, a source of UV (or other wavelength) radiation that will be transmitted through the segment/abutment and be bacteriocidal/bacteriostatic to the bacteria adjacent to the segment/abutment. The bacteria may need to be sensitized to the wavelength of radiation chosen, in which case a photosensitizing substance may be introduced into the gingival crevice as an adjunct to this procedure.

Antibiofilm Segment/Abutment:

A segment or abutment can be removed and treated every 3 months (or less frequently depending on the antibiofilm activity of the applied material) with a retentive, hardening fluid that has antibacterial or antibiofilm properties. This substance may dissolve or lose activity over time in which case it may need to be reapplied at varying intervals. The abutment will be dipped in the fluid phase of this substance which will be allowed to dry, or harden or can be baked or formed in place as either a liquid or powder. This abutment will then be replaced onto the fixture. This surface material will contain antibiotics/antibacterials that will keep the peri-implant crevice free of biofilm, especially on the surface of the implant that is covered with the anti-infective material.

Quick Disconnect Abutment:

The quick disconnect abutment provides for simple, quick, easy, removal of the crown and all TGP components of the implant for cleaning by both the clinician (periodically) and the patient (daily or more often). In this design, all (or almost all) of the biofilm susceptible structures (the TGP) of the implant and restoration can be removed easily and frequently by both the clinician and the patient which would preclude any significant bacterial growth and disease.

Figure 27:
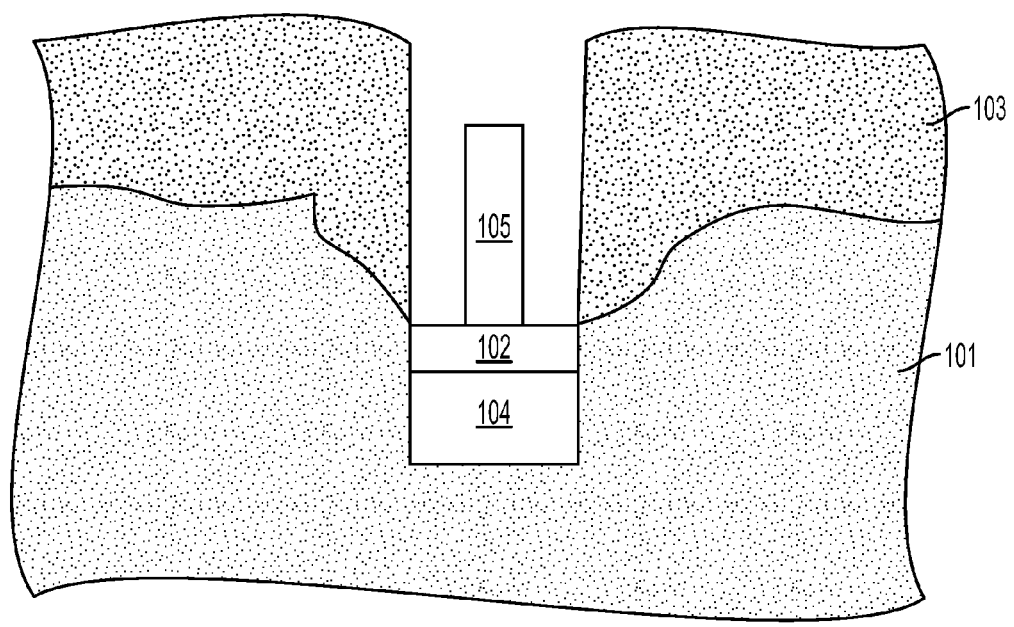
FIG. 27 is a diagram showing a core prior to attachment of an embodiment of the quick disconnect assembly design.
Figure 28:
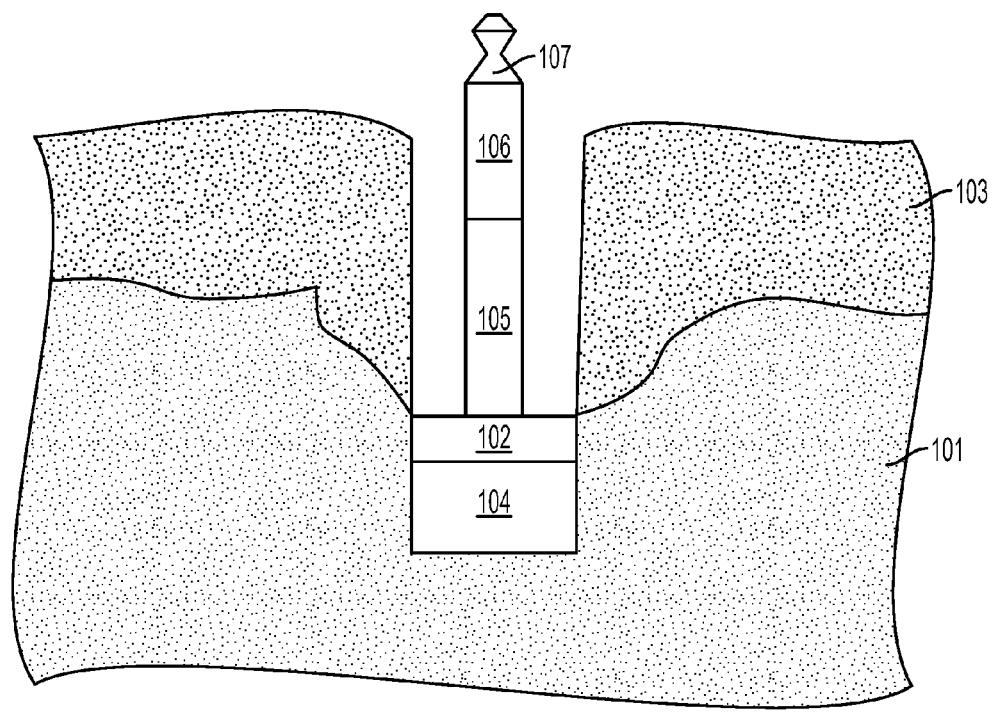
FIG. 28 depicts attachment of the quick disconnect male portion onto the core.
Figure 28A:
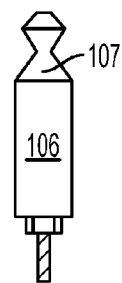
FIG. 28A depicts the mechanism for attaching the quick disconnect male portion to the core of FIG. 28.

As shown in FIG. 27, due to loss of bone 101, various segments 102 have been removed down to the osseous crest where the gum 103 meets the bone 101. Thus, as shown in FIG. 27, only a single segment 102 and the base 104 remain on the core 105. Then, as shown in FIG. 28, a quick disconnect male portion 106 is attached to the core 105. The quick disconnect male portion 106 may be screwed into the core (see FIG. 28A). Any other suitable means of connecting the quick disconnect male portion 106 with the core 105 may be used. Also, as shown, the quick disconnect male portion 106 has a narrowed neck portion 107.

Figure 29:
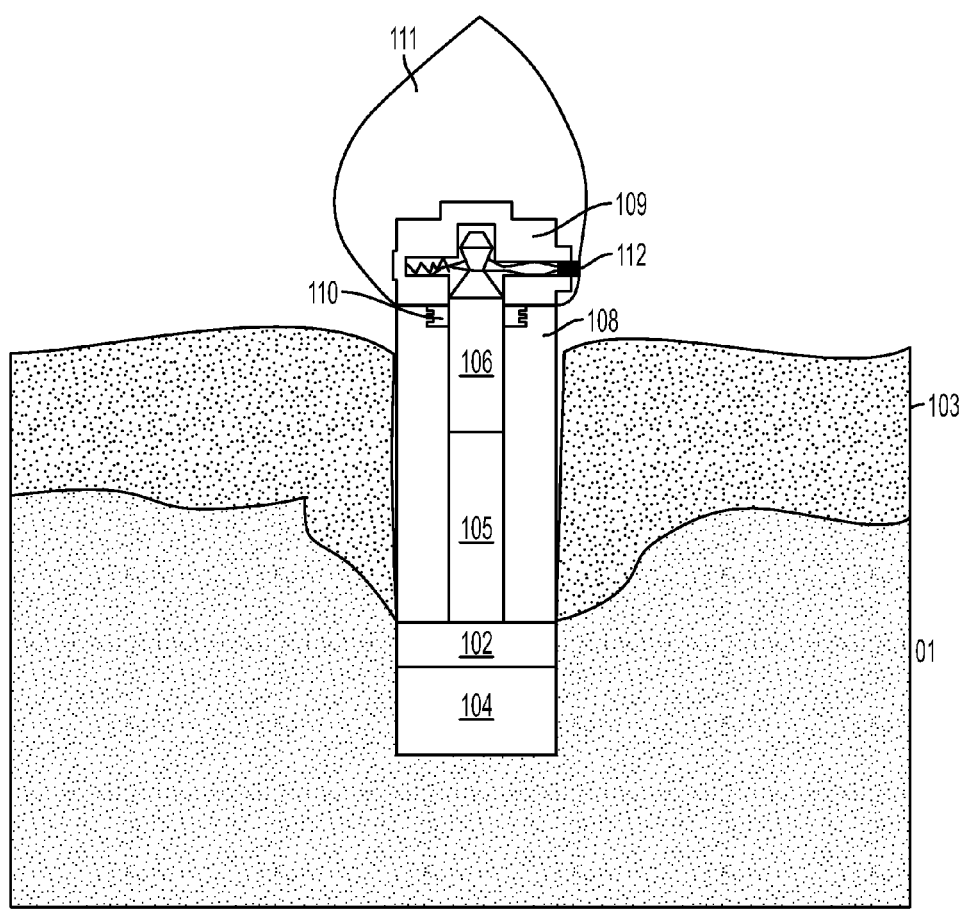
FIG. 29 depicts attachment of the quick disconnect female portion to the quick disconnect male portion.

After attaching the quick disconnect male portion 106 to the core 105, a segment replacement section 108 is slid over the exposed core 105 and the quick disconnect male portion 106 (see FIG. 29). The quick disconnect female portion 109 is then attached to the segment replacement section 108 using a threaded connector portion 110. Alternatively, the segment replacement section 108 and the quick disconnect female portion 109 can be formed as a single unit. As also shown in FIG. 29, a crown 111 is baked onto the quick disconnect female portion 109. The crown 11 can be formed of standard materials used to fabricate dental restorations, e.g., porcelain or castable ceramics.

Figure 30:
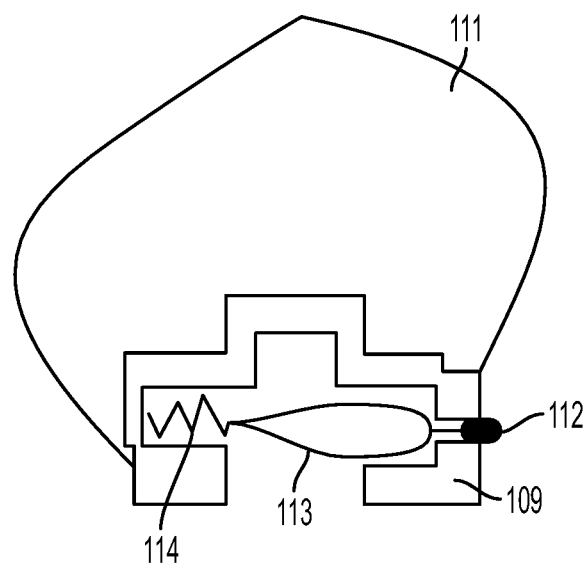
FIG. 30 is a close-up view of the quick disconnect female portion with crown attached.
Figure 31:
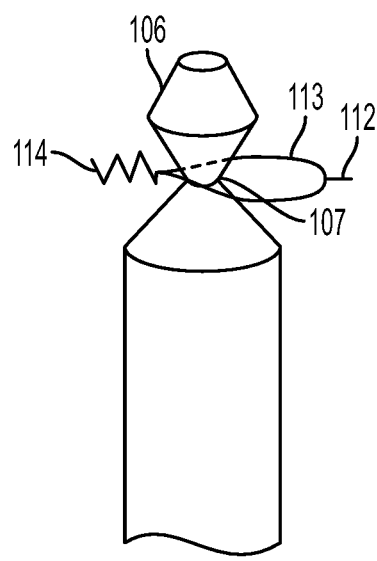
FIG. 31 is a simplified view showing the connection between the retention ring of the quick disconnect female portion and the quick disconnect male portion.

Simplified views of the elements provided within the quick disconnect female portion 109 are provided in FIGS. 30 and 31. As shown in FIG. 30, the quick disconnect female portion 109 includes an actuator button 112, a retention ring 113 and a spring 114. The connection between the retention ring 113 and the quick disconnect male portion 106 is shown in FIG. 31. The actuator button 112 is provided with a seal or precise fit to prevent food and bacteria intrusion. When the actuator button 112 is not pressed, the force of the spring 114 maintains the narrow diameter portion of the retention ring 113 to remain around the narrowed neck portion 107 of the quick disconnect male portion 106. By pressing the actuator button 112, the spring 114 is compressed to move the retention ring 113 sideways, such that the larger diameter portion of the retention ring 113 moves into position around the narrowed neck portion 107 of the quick disconnect male portion 106. This allows the quick disconnect female portion 109 to become disengaged from the quick disconnect male portion 106.

Figure 32:
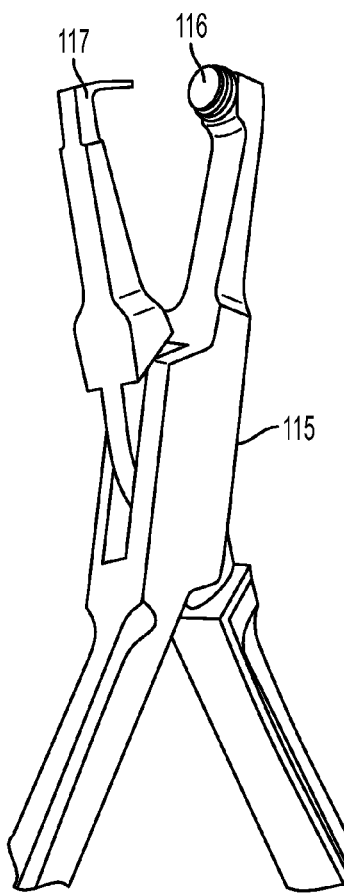
FIG. 32 depicts an embodiment of plyers having a pin for actuating a quick disconnect button.
Figure 33:
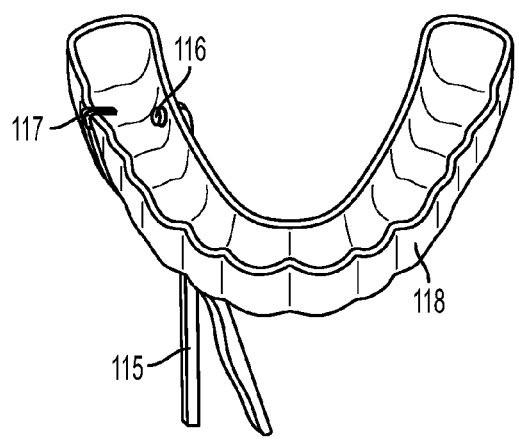
FIG. 33 depicts a tray for use with the plyers of FIG. 32.

The quick disconnect female portion 109 and crown 111 attached thereto would then be soaked in bleach or other anti-infective agent for a suitable period of time, such as 20 minutes, to sterilize/disinfect it. The remaining structures in the mouth would be cleaned, and then the quick disconnect female portion 109 and crown 111 attached thereto would be pushed back into place with a "click". This removal and cleaning would be simple to perform by the clinician using a plyers 115 (see FIG. 32) that would hold the quick disconnect female portion 109 on one side using a retention pad 116 while pressing the actuator button 112 on the other side using a pin 117. As shown in FIG. 33, a tray 118 can be provided in connection with the plyers 115. The tray 118 enables a patient or clinician to determine the proper placement of the plyers 115 with respect to the actuator button 112 for crown removal. The plyers 115 can also be formed integral with the tray 118, as shown in FIG. 33. In use, the patient (or clinician) places the tray 118 in their mouth with correct orientation in relation to the teeth. This would then index the integral plyers 115 in the precise location to be able to actuate the actuator button 112. In addition, the tray 118 provides for a simple means of replacing the crown 111 back in the mouth after cleaning in the correct orientation and location.

A similar design as discussed above can be incorporated into a multi-unit bridge anchored to several implants. If the restoration in question were a multi-unit bridge supported by several implants, the plyers discussed above would be inadequate to remove this extensive and highly complex Bridge. To address this issue, a hard acrylic tray would be provided that is similar to tray 118 shown in FIG. 33. Built into this tray would be a mechanism with one piston adjacent to each actuator button. Therefore, there would be multiple pistons corresponding to each actuator button in a multi-unit scenario. When the clinician or patient desires to remove the multiunit restoration or bridge, the tray would be inserted into the mouth, and all the pistons would be activated simultaneously by a plyer type handle built into the tray. The tray would then be removed from the mouth with the multi-unit restoration or bridge embedded in it. The entire tray and restoration unit is then immersed in cleaning solution and the implant sites are cleaned. Once cleaning is completed, the entire tray would be inserted into the mouth, and the handle would be deactivated which would reengage all the implant fixtures. The tray is then removed from the mouth leaving the entire restoration retained in the mouth. This tray has several benefits: 1) simultaneous pin activation, 2) correctly orients the restoration in all degrees of freedom, 3) retains the restoration during removal and insertion to prevent lose or aspiration by the patient.

Figure 34:
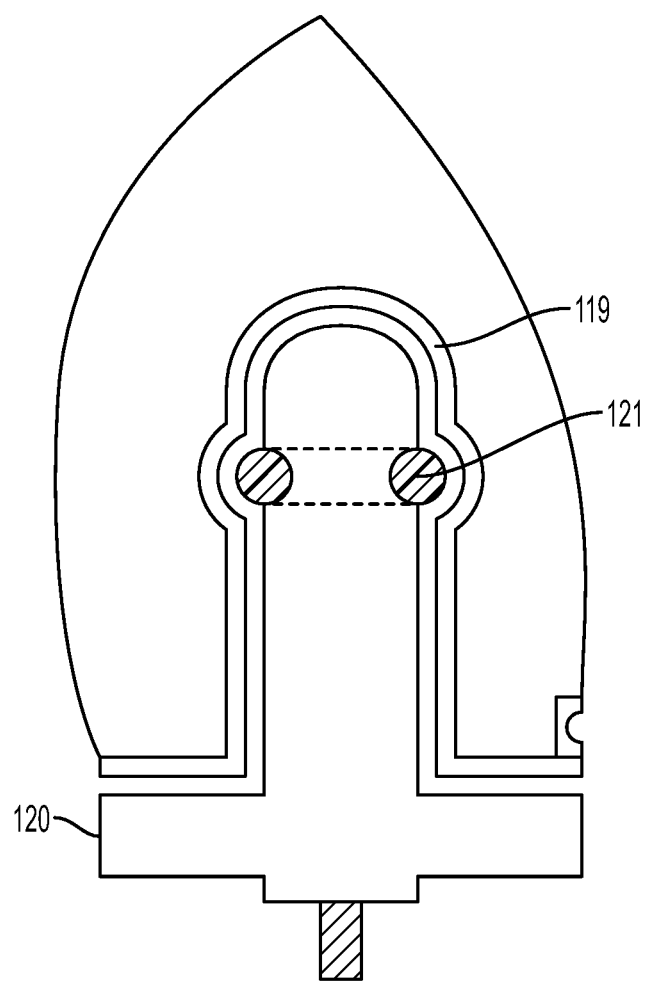
FIG. 34 depicts an alternate embodiment of the quick disconnect design.

FIG. 34 depicts an alternate embodiment of the quick disconnect design. Rather than use the retention ring 113 and the spring 114, etc., the alternate embodiment connects a quick disconnect female portion 119 to a male quick disconnect portion 120 using an o-ring 121. The o-ring 121 acts as a retention mechanism.

A system and method to retrofit infected single piece conventional implant fixtures is discussed below.

In the present Application, removal of individual infected implant portions is possible. There still exists, however, many conventional single-unit implant fixtures that are subject to the ravages of peri-implantitis. To address this issue, the following systems and methods can be used:

Overview: A system and method to remove the outer layer of the supraosseous portion of an existing implant such that this removed layer allows placement of a removable sleeve that can be easily cleaned by the clinician or that is made of (or coated with) an antibiofilm material, such as the material provided by Agion® technology.

The system is comprised of the following: A device (not shown) that will attach to adjacent teeth or adjacent implants to provide a rigid, indexible position. Such device will assist the clinician in analyzing the subject infected implant and align the cutting device precisely along the long access of the implant. The device will have a end cutting trephine drill as described above that will precisely remove the outer 0.5 mm (or other amount) of titanium implant surface that may include all threads on the entire supraosseous surface. The device will have an irrigation system to water cool the implant and cutting instrument.

Sleeves: Various sizes of sleeves are part of this system. These sleeves will precisely fit the trimmed conventional implant discussed above and be retained by the abutment placed over the implant.

Method: When a clinician diagnoses an infected conventional single piece implant, the clinician will reflect a surgical flap and place the indexed and aligned end cutting trephine drill. The device will then remove 0.5 mm thickness over the entire surface of the infected implant surface. A sterile removable sleeve will then be placed over the trimmed implant. This sleeve can be removable and cleanable/sterilizable and/or manufactured with a surface that contains antibiofilm properties. The abutment and restoration will then be removably attached. The patient will be taught proper oral hygiene techniques. Every 3 months, the restoration, abutment and sleeve can be removed, sterilized and then put back into place if deemed necessary by the clinician. This constant cleaning will preclude any further bone loss associated with biofilm in the area. In the case of an antibiofilm surface material, the sleeve may not be required to be removed and cleaned/replaced unless the material has been depleted of its antibiofilm properties or if the site has reinfected for some other reason.

A variation on this is to disinfect the implant surface, place an antibacterial substance inside a custom-fit sleeve that will slowly leech out over time, and put the sleeve (removably) into place. A seal of sorts may be necessary at the apical and/or coronal extent of the sleeve to prevent external toxic material and/or bacteria from having access to the covered implant surface as well as to prevent bacteria and toxic material from the implant surface to leech out and affect the surrounding tissue. The sleeve surface will represent the new surface that would be colonized by biofilm, but this sleeve would be removed as necessary for cleaning, sterilization and/or replacement, e.g., every 3 months.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method for treating an infection of a modular dental implant, the dental implant including a distal base and a plurality of segments removably attached to the base for implantation of the segments in contact with jawbone, with an internal channel that extends through the plurality of segments, the method comprising:
   diagnosing infection around an implant site of the dental implant and determining if at least one segment, out of the plurality of segments, is affected by the infection;
   providing a flow of fluid into the dental implant via said internal channel;
   extracting the infected segment from the dental implant while maintaining positioning of uninfected segments and the base; and
   replacing the infected segment with at least one cleaned or sterilized segment.

2. The method according to claim 1, wherein the dental implant further includes a core removably attached to the base, the plurality of segments being removably attached to at least one of the base and the core.

3. The method according to claim 1, wherein the dental implant further includes a core permanently attached to the base, the plurality of segments being removably attached to at least one of the base and the core.

4. The method according to claim 1, wherein the at least one cleaned or sterilized segment comprises either the extracted infected segment that has been cleaned and/or sterilized or new sterile segments.

5. The method according to claim 1, further comprising providing bone grafting material at the replacement site of the at least one cleaned or sterilized segment or on the outer surface of the at least one cleaned or sterilized segment to facilitate bone regrowth and/or osseointegration of the at least one cleaned or sterilized segment within the jawbone of a patient.

6. The method according to claim 1, further comprising determining a number of cleaned or sterilized segments to replace the at least one infected segment based on an amount of bone regrowth and/or osseointegration to occur at the implant site.

7. The method according to claim 1, wherein an abutment, which retains a crown or restoration of the dental implant or is integral with the crown or restoration of the dental implant, is removably attached to one of an uppermost segment section and a core, and prior to extraction of the infected segments, the crown and abutment are removed.

8. The method according to claim 1, wherein:
at least a first segment is structured to permit separation in a proximal direction from engagement with a distally disposed second segment without requiring rotation of the first segment with respect to the second segment.

9. The method according to claim 1, further comprising using an end cutting trephine drill to remove bone around a partially osseointegrated segment to facilitate removal thereof.

10. The method according to claim 9, wherein the end cutting trephine drill is provided with fluid channels that cause a fluid to flow from ports provided therein during bone removal.

11. The method according to claim 1, wherein at least one of the plurality of segments is attached to an abutment, the abutment configured for attachment with or configured integrally with a crown or other restoration, such that the at least one segment and abutment are extracted with the artificial crown or other restoration for cleaning and/or sterilization.

12. A dental implant to be inserted into a jawbone of a patient comprising:
a base segment provided at one distal end of the implant, the base segment configured to be placed inside at least one of the jawbone and bone graft material;
a plurality of removable segments which are configured to be put inside and come in contact with at least one of the jawbone and the bone graft material and are removably attached to the base segment
an internal fluid channel that extends through the plurality of removable segments to allow the flow of fluid through the dental implant; and
an abutment portion provided on an end of the implant that is opposite to the one distal end,
wherein the abutment portion is configured for attachment with an artificial tooth or is formed integrally with the artificial tooth, and
wherein, the removable segments extend between the base segment and the abutment portion.

13. The dental implant according to claim 12, further comprising a core removably attached to the base segment at one end and removably attached to the abutment portion at an end opposite to the one end,
wherein the plurality of removable segments are formed as segments that respectively surround the core.

14. The dental implant according to claim 13, wherein the core is provided with at least one slot on an exterior surface thereof, the at least one slot formed to mate with at least one protrusion provided on an interior surface of each of the plurality of removable segments, such that the protrusions slide within the slots during attachment of the removable segments to the core or during detachment of the removable segments from the core.

15. The dental implant according to claim 13, wherein the core is provided with a keyed surface comprising a plurality of longitudinal grooves that mate with at least one protrusion provided to an interior surface of each of the plurality of removable segments, such that an orientation of the removable segments with respect to the core is variable.

16. The dental implant according to claim 13, further comprising a male disconnect portion attached to the end of the core to which the abutment portion is attached, such that the male disconnect portion is attached between the core and the abutment portion, wherein the abutment portion forms a female disconnect portion that is releasably connected to the male disconnect portion.

17. The dental implant according to claim 16, wherein the female disconnect portion includes an actuator button that releases the connection to the male disconnect portion.

18. The dental implant according to claim 17, wherein the actuator button is connected to a retention ring that surrounds an end portion of the male disconnect portion, the retention ring having a narrow diameter portion that retains the end portion of the male disconnect portion,
wherein, a spring, in a non-compressed state, maintains the connection between the narrow diameter portion of the retention ring and the end portion of the male disconnect portion, and
when the actuator button is pressed, the spring is compressed to release the connection between the narrow diameter portion of the retention ring and the end portion of the male disconnect portion to allow removal of the female disconnect portion and the artificial tooth attached thereto.

19. The dental implant according to claim 12, wherein outer surfaces of the base segment and the removable segments are provided with tissue growth management material to promote selective growth and ingrowth of bone, connective tissue and epithelial attachment.

20. The dental implant according to claim 19, wherein one or more of the outer surfaces of the base segment and the removable segments are sintered or polished.

21. The dental implant according to claim 12, wherein the base segment and the removable segments are provided with an anti-rotation device that restricts rotation of the base segment and a removable segment with respect to each other.

22. The dental implant according to claim 21, wherein the anti-rotation device is comprised of protrusions provided on either a bottom surface or an upper surface of each removable segment, the protrusions being formed to mate with respective holes provided on the other of the bottom surface and the upper surface of the base segment and each removable segment.

23. The dental implant according to claim 22, wherein the protrusions and corresponding holes are cone shaped.

24. The dental implant according to claim 12, wherein an inner surface of a segment formed by the uppermost removable segment is threaded to engage with corresponding threads provided on an external surface of the upper end of the core.

25. The dental implant according to claim 12, wherein the removable segments that are provided closer to the abutment portion than to the base segment are tapered, such that upper removable segments taper down towards lower removable segments having a constant width.

26. The dental implant according to claim 12, wherein each removable segment is comprised of an upper cylindrical collar portion and a lower tapered portion, the lower tapered portion of each removable segment configured to nest within the collar portion of an adjacent removable segment when the removable segments are arranged longitudinally.

27. The dental implant according to claim 12, wherein:
at least a first segment is structured to permit separation in a proximal direction from engagement with a distally disposed second segment without requiring rotation of the first segment with respect to the second segment.

28. The dental implant according to claim 12, wherein the base segment and/or one or more of the segments have a polished outer surface to prevent osseointegration and/or facilitate debris removal.

29. The dental implant according to claim 12, wherein the at least one surface of the base segment is polished or formed or coated with a material that is not conducive to osseointegration.

30. The dental implant according to claim 29, wherein the material that forms at least one of the surfaces of the base segment is stainless steel or polytetrafluoroethelyne.

31. The dental implant according to claim 12, wherein at least two base segments are provided, each base segment including the plurality of removable segments and the abutment portion, respectively,
wherein at least two abutment portions are configured to attach to a bridge comprising at least two artificial teeth that are connected side by side.

32. The dental implant according to claim 31, wherein a respective screw is provided to retain each end of the bridge to a corresponding abutment portion.

33. The dental implant according to claim 12, wherein at least one of the removable segments is a variable length segment having a plurality of slots cut circumferentially into an exterior face thereof, the slots being spaced apart from one another by a predetermined distance,
wherein the slots form a cutting position for the length of the variable length segment to be modified.

34. In combination with the dental implant according to claim 33, a variable length segment cutting tool that cuts a variable length segment, the cutting tool comprising a jig that retains the variable length segment and a cutting disc maintained in relation to the jig, the cutting disc configured to cut the variable length segment along the slots provided on the exterior face thereof to modify the length of the variable length segment.

35. In combination with the dental implant according to claim 33, a variable length segment indexing tool that measures a cutting amount of a variable length segment, the indexing tool comprising:
a bolt that screws into a core removably attached to the base segment;
a plate attached to the bolt, the plate positioned at the coronal extent of the core; and
a measuring rod that measures the distance between the plate and the coronal extent of the base and any remaining segments,
wherein the measured distance is used to determine the cutting amount of the variable length segment.

36. In combination with the dental implant according to claim 12, a segment removal tool that removes the plurality of removable segments.

37. The combination according to claim 36, wherein the removal tool comprises a substantially cylindrical body that fits over at least one of the removable segments, an internal surface of the cylindrical body provided with threads that engage with threads provided on an external surface of the removable segments.

38. The combination according to claim 36, wherein the removal tool comprises prongs that engage with slots provided in at least one of the removable segments.

* * * * *